United States Patent
Sher

(10) Patent No.: US 7,670,288 B2
(45) Date of Patent: Mar. 2, 2010

(54) FLUCTUATING BLOOD GLUCOSE NOTIFICATION THRESHOLD PROFILES AND METHODS OF USE

(76) Inventor: Philip M. Sher, 18 Mifflin Ct., Plainsboro, NJ (US) 08536

( * ) Notice: Subject to any disclaimer, the term of this patent is extended or adjusted under 35 U.S.C. 154(b) by 712 days.

(21) Appl. No.: 10/589,211

(22) PCT Filed: Jun. 8, 2006

(86) PCT No.: PCT/US2006/022254

§ 371 (c)(1),
(2), (4) Date: Aug. 11, 2006

(87) PCT Pub. No.: WO2006/133348

PCT Pub. Date: Dec. 14, 2006

(65) Prior Publication Data

US 2008/0228055 A1    Sep. 18, 2008

Related U.S. Application Data

(60) Provisional application No. 60/688,470, filed on Jun. 8, 2005.

(51) Int. Cl.
*A61B 5/00* (2006.01)
(52) U.S. Cl. .................... 600/365; 600/345; 600/347
(58) Field of Classification Search .................. 600/347, 600/345, 300, 365
See application file for complete search history.

(56) References Cited

U.S. PATENT DOCUMENTS

| | | | |
|---|---|---|---|
| 5,464,012 A | 11/1995 | Falcone | |
| 5,791,344 A | 8/1998 | Schulman et al. | |
| 5,800,420 A | 9/1998 | Gross et al. | |
| 6,049,727 A | 4/2000 | Crothall | |
| 6,126,595 A | 10/2000 | Amano et al. | |
| 6,241,661 B1 | 6/2001 | Schluess et al. | |
| 6,556,957 B1 | 4/2003 | Daumer | |
| 7,079,035 B2 | 7/2006 | Bock et al. | |
| 7,123,950 B2 | 10/2006 | Mannheimer | |
| 7,200,253 B2 * | 4/2007 | Glukhovsky et al. | 382/128 |
| 2001/0011224 A1 | 8/2001 | Brown | |
| 2002/0082487 A1 | 6/2002 | Kollias et al. | |

(Continued)

FOREIGN PATENT DOCUMENTS

| | | |
|---|---|---|
| WO | WO03000127 | 1/2003 |
| WO | WO 03/023356 | 3/2003 |

OTHER PUBLICATIONS

Edward J. Knobbe and Bruce Buckingham, The extended kalman filter for continuous glucose monitoring, Diabetes Technology & Therapeutics, vol. 7, No. 1, 2005, pp. 15-27.

(Continued)

*Primary Examiner*—Robert L Nasser
*Assistant Examiner*—Michael D'Angelo
(74) *Attorney, Agent, or Firm*—Altimatia, LLC; David M. Gange

(57) ABSTRACT

Embodiments of the present invention provide a new system and methods for monitoring blood glucose concentration. A user of a continuous glucose monitor may program upper and lower blood glucose notification thresholds to fluctuate over time in order to facilitate management of the short-term effects of food consumption, insulin delivery aberrations, physical activity, emotions, and unforeseen circumstances.

36 Claims, 13 Drawing Sheets

U.S. PATENT DOCUMENTS

| | | |
|---|---|---|
| 2003/0028089 A1* | 2/2003 | Galley et al. ............... 600/365 |
| 2003/0108976 A1 | 6/2003 | Braig et al. |
| 2003/0125612 A1 | 7/2003 | Fox et al. |
| 2003/0137423 A1 | 7/2003 | Al-Ali |
| 2003/0176933 A1 | 9/2003 | Lebel et al. |
| 2003/0191376 A1 | 10/2003 | Samuels et al. |
| 2004/0044272 A1 | 3/2004 | Moerman et al. |
| 2004/0153257 A1 | 8/2004 | Munk |
| 2005/0004439 A1* | 1/2005 | Shin et al. ................. 600/365 |
| 2005/0038332 A1* | 2/2005 | Saidara et al. ............. 600/347 |
| 2005/0090726 A1 | 4/2005 | Ackerman |
| 2005/0096512 A1* | 5/2005 | Fox et al. ................... 600/300 |
| 2005/0199494 A1 | 9/2005 | Say et al. |
| 2007/0276209 A1 | 11/2007 | Emoto et al. |

OTHER PUBLICATIONS

Satish K. Garg, Sherwyn Schwartz, Steven V. Edelman, Imp. Gluc. Excursions Using an Implantable RT Cont. Gluc. Snsr in Adults w/ Type 1 Diab., Diab. Care, vol. 27, No. 3, 2004.

* cited by examiner

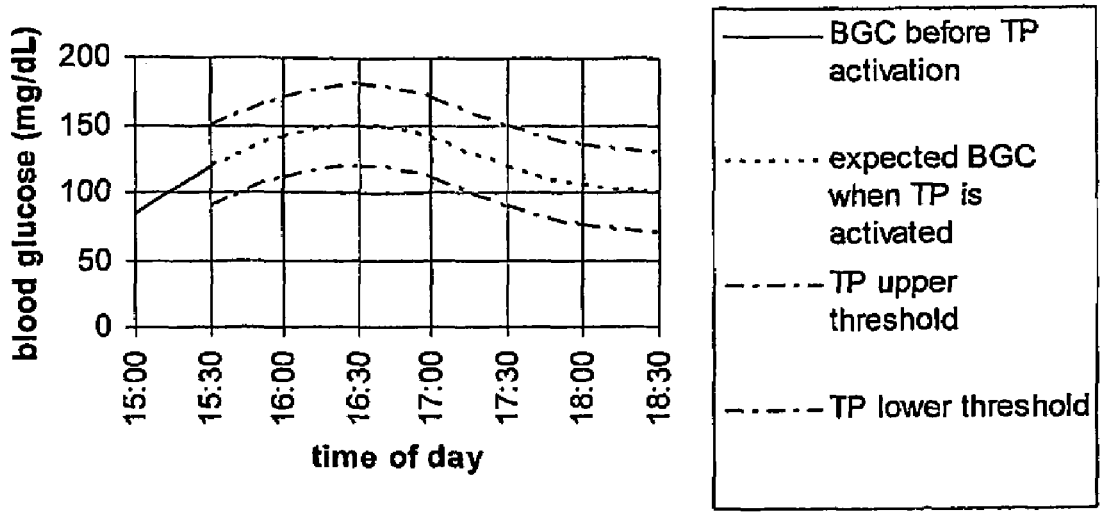
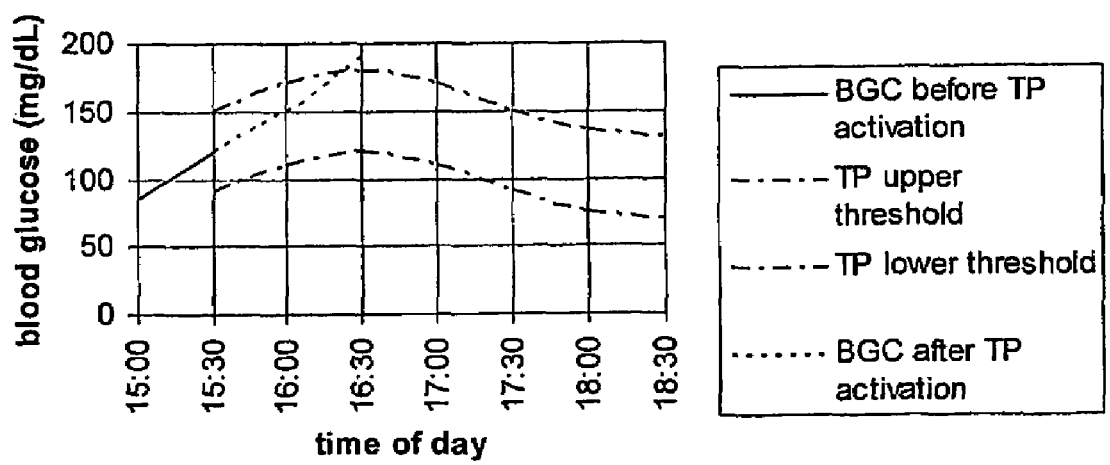

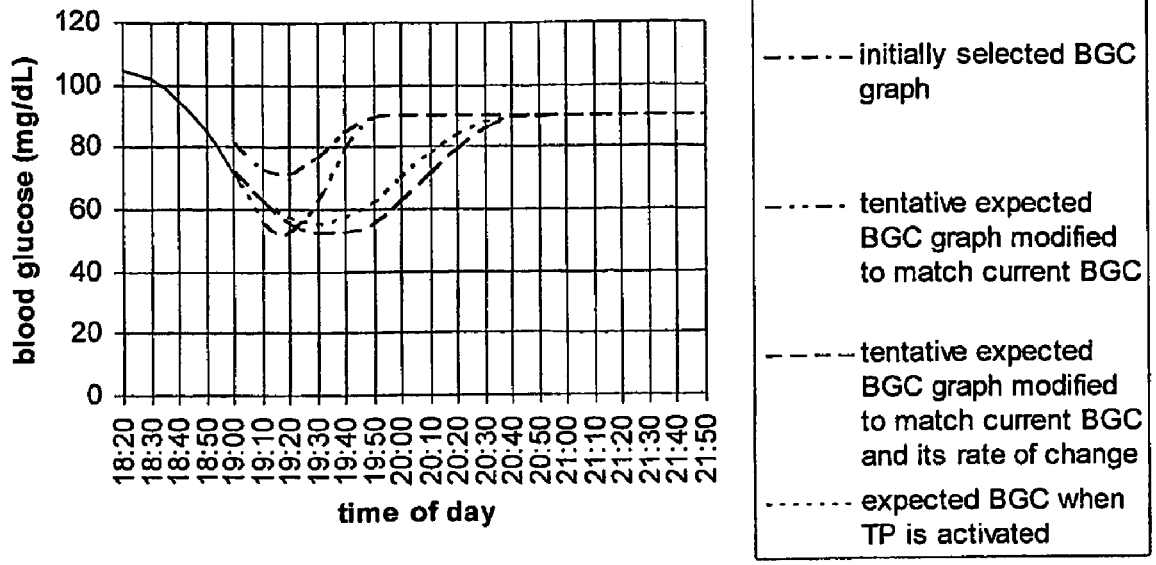
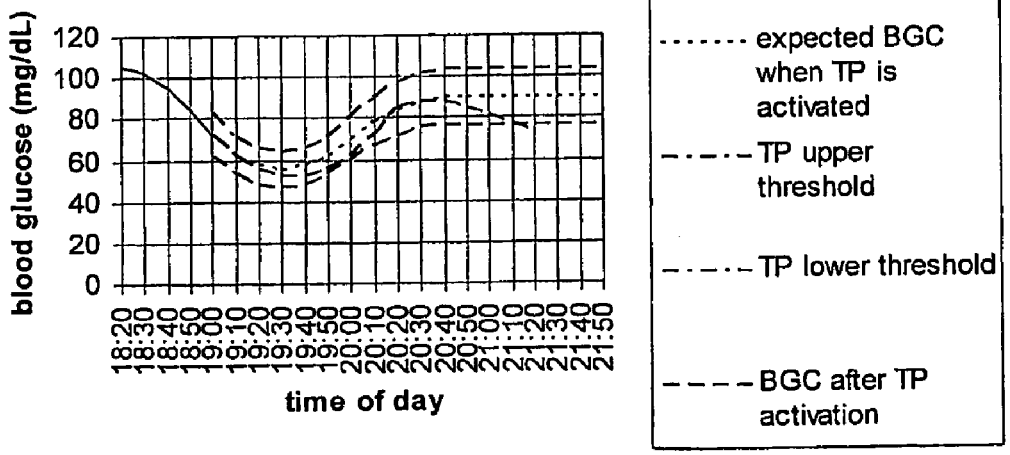

FLUCTUATING BLOOD GLUCOSE NOTIFICATION THRESHOLD PROFILES AND METHODS OF USE

CROSS REFERENCE TO RELATED APPLICATIONS

This application claims the benefit of U.S. Provisional Patent Application Ser. No. 60/688,470, filed Jun. 8, 2005.

FIELD

Embodiments of the invention relate to a system and methods for monitoring the level of blood glucose in a diabetes patient wherein a user may adjust upper and lower thresholds of blood glucose concentration that trigger notifications to the user. Embodiments of the invention for the first time provide a method for the user to establish fluctuating upper and lower blood glucose concentration notification thresholds to manage the short-term effects of food consumption, insulin delivery aberrations, physical activity, emotions, and unforeseen circumstances.

BACKGROUND

It is now a well established principle of diabetes care that in order to prevent, delay, and/or reduce the complications of diabetes, it is desirable to maintain, as much of the time as possible, a blood glucose concentration (BGC) within or close to the normal range. Yet, at present, for individuals who must use exogenous insulin, the goal of maintaining euglycemia or near euglycemia a large fraction of the time is difficult or impossible. While subcutaneous insulin therapy empowers the patient to decrease BGC very effectively, the risk of hypoglycemia from too much exogenous insulin forces patients to frequently use too little insulin. As a result, most patients experience higher than normal average BGC with occasional episodes of both very high and very low BGC. Maintaining continuous euglycemia is challenging because it requires balancing the intensity of self-administered, subcutaneous insulin's action with the insulin action required to keep BGC steady, and to do so continuously on a timescale of less than one hour. Since several factors that can only be estimated impact this balance, even the most diligent and capable individuals using the best technology available cannot prevent their BGC from occasionally straying outside of the normal range. When testing reveals that BGC is too high or too low, corrective measures can be taken to reestablish euglycemia. Continuous blood glucose concentration data provides the fastest possible indication that corrective measures should be taken, and therefore, continuous glucose monitors were predicted to be particularly useful for optimizing blood glucose control.

In the first long-term study in which real-time, continuous blood glucose concentration data was available to insulin-using individuals with type I diabetes in the home setting (Diabetes Care, March 2004, pp. 734-738), blood glucose control was significantly better than when the same patients relied only on conventional, periodic blood glucose testing. With access to continuous data, patients spent 88% more time with their BGC in the 80-140 mg/dL (euglycemic) range, 47% less time with their BGC below 56 mg/dL, and 25% less time with their BGC above 239 mg/dL. However, even though blood glucose control was greatly improved by access to continuous blood glucose concentration data, these patients still spent only 9 hours per day with their BGC in the 80-140 mg/dL range, and they spent 7 hours per day with their BGC either below 56 mg/dL or above 239 mg/dL. Clearly, continuous blood glucose monitors can help improve blood glucose control, but access to continuous blood glucose concentration data alone is not sufficient to enable most patients to maintain euglycemia or near euglycemia as much of the time as would be ideal.

An important factor that limits blood glucose control and which is inherent to subcutaneous insulin therapy is the lag time between the delivery of subcutaneous insulin and its action. The fact that in order to maintain euglycemia after a meal, even the fastest insulin analogs should be dosed subcutaneously approximately 15 minutes before the meal, means that forethought is required to provide timely exogenous insulin action. Often, such forethought is not practical or is not exercised for other reasons, and a high BGC after a meal results. However, the need for forethought is not the only difficulty stemming from subcutaneous insulin's lag time. The combination of the lag time and the difficulty of knowing precisely how much insulin is required greatly complicates blood glucose control. The amount of exogenous insulin needed can only be estimated because it is a function of variables that typically are not precisely known—namely, insulin sensitivity, food quantity and composition, physical activity level, the amount of insulin already in the subcutaneous tissue and blood, and the blood concentrations of other hormones. Were it not for subcutaneous insulin's lag time, it would be theoretically possible to closely control BGC, even without knowing in advance exactly how much insulin is required, by repeatedly dosing small amounts of insulin subcutaneously when, and only when, continuous blood glucose data indicates a higher than desired BGC. In fact, a healthy pancreas, which delivers insulin directly into the bloodstream, and therefore with minimal lag time, in response to its own continuous blood glucose sensing, controls BGC in this manner, albeit aided by additional signaling pathways. However, the fact of the lag time of subcutaneous insulin action, means that even continuous glucose data cannot provide truly timely feedback on whether the amount of insulin already dosed is correct. Therefore, whether insulin is administered by injections or with an insulin pump, even with the benefit of a continuous glucose monitor, it is still desirable for the patient to develop the skill of gauging how much insulin to administer and when to administer it, and it is still the case that BGC will occasionally stray out of the normal range such that the patient will need to manage a quick and safe return to euglycemia.

Among the many, commonly encountered situations in which BGC has strayed or will stray outside of the target range are situations in which an insulin delivery problem has occurred, situations in which an insulin pump and continuous glucose monitor have been removed to participate in athletics, situations in which insulin has not been administered until after a child, who does not eat predictably, has eaten, situations in which a food that raises BGC rapidly has been eaten too soon after insulin administration, situations in which the carbohydrate content of a food has been underestimated or overestimated, situations in which an abnormally high BGC has been corrected with excessive insulin, situations in which the effect of exercise on BGC has been incorrectly estimated, situations in which stress has resulted in an unanticipated increase of BGC, and situations in which in the pharmacodynamic profile of insulin administered does not match optimal insulin action in the aftermath of a meal.

Embodiments of the invention described herein comprise new features of a continuous glucose monitor and methods for their use. These new features are designed to aid a user in managing situations in which BGC has strayed or will stray outside of the normal or target range and also to enhance the user's skill of predicting how BGC will respond to the various factors that affect it. Specifically, embodiments of the invention relate to notifications that a continuous glucose monitor provides to a user as a function of BGC and the criteria that trigger those notifications.

DESCRIPTION OF THE RELATED ART

The following references disclose the art relevant to embodiments of the present invention: US 2005/038332, US 2002/082487, U.S. Pat. No. 5,800,420, US 2004/044272, US 2005/199494, US 2001/011224, U.S. Pat. No. 5,791,344, US 2004/153257, WO 2003/000127, US 2003/191376, U.S. Pat. No. 6,049,727, WO 2003/023356, and US 2003/176933. These references, provisional application 60/688,470, and other references cited within this application are hereby incorporated herein by reference.

The art offers several descriptions of notifications that blood glucose monitors, both continuous and otherwise, may provide to their users. Notifications are typically alarms that may be auditory, visual, tactile, etc. The most thoroughly described purpose of an alarm is to alert a user to hypoglycemia or to warn the user of impending hypoglycemia. Likewise, hyperglycemia and impending hyperglycemia can trigger an alarm according to some disclosures.

According to the art, an obvious advantage of an alarm is that it frees a user from having to frequently view the monitor's display to see if BGC is unacceptably high or low or if it appears as though BGC will soon become unacceptably high or low. This is a convenience when the user is awake and a near necessity when the user is asleep. Among the criteria that art devices employ to trigger an alarm are a BGC that is above or below predetermined thresholds, and/or a rate of change of BGC that is above or below predetermined thresholds, and/or a percentage rate of change of BGC that is above or below predetermined thresholds, and/or a second derivative of BGC over time that is above or below predetermined thresholds, and/or other BGC-related criteria according to specifically designed, predetermined algorithms.

These alarm criteria can all be set by the device manufacturer, and optionally with input from a healthcare provider, the BGC thresholds and rate of change thresholds may be customized and set by a user. If customized, these thresholds may be adjusted by the user by pressing buttons on the device. These alarm triggering thresholds may be displayed on the device in numerical or graphical form along with recent and present blood glucose and blood glucose rate of change data. A user may set the BGC thresholds to different values at different times of day according to a predetermined schedule. For instance, according to the art, a user may program one threshold value for when he is generally awake and another for when he is generally asleep. However, except for such predetermined threshold variation, the art BGC alarm thresholds are static. There is no suggestion in the art that BGC thresholds may change continuously with time (as opposed to changing in a step-wise fashion according to a predetermined schedule) or that they should be changed based on the dynamics of a current situation. A user manages BGC, according to the art, by taking measures in response to alarms, but not by changing the BGC thresholds that trigger alarms. In response to an alarm, a user may adjust BGC by administration of insulin or consumption of carbohydrate. In addition, the alarm status of the device must be managed. An alarm may automatically deactivate after a set period of time or it may deactivate when the alarming condition no longer exists. To prevent redundant and excessive alarms, when an alarm occurs, a user or the device automatically may set a timer/reminder function that temporarily disables the alarm system or temporarily partially disables the alarm system so that continuation of the condition that triggered the alarm does not cause additional, identical alarms for a finite period of time. Upon expiration of this period, the alarm system fully reactivates and the user may be promoted to take additional measures, such as rechecking for the condition that caused the alarm. A user may also temporarily deactivate an alarm preemptively. To reiterate, there is no suggestion in the art that BGC thresholds may change continuously with time or that they should be changed based on the dynamics of a current situation. According to the art, a user manages BGC by taking measures in response to alarms and optionally by disabling alarms, but not by changing the BGC thresholds that trigger alarms.

For the sake of clarity, it is worthwhile to distinguish between a BGC threshold that may change continuously over time, which is not disclosed in the art, and a threshold for a rate of change of BGC, which is disclosed in the art. These are different both in concept and in practice. Even though a rate of change of BGC implies a BGC that changes continuously over time, a threshold defined by a BGC value that may change continuously over time, as in embodiments of the present invention, cannot generally be duplicated by a threshold defined by a rate of change of BGC or any other art alarm threshold option or combination of options.

Overall, the art alarm features seem well-designed for detecting and alerting a user to hypoglycemia or hyperglycemia or impending hypoglycemia or hyperglycemia when BGC begins within or near the target range. However, the art alarm features seem less helpful for managing a quick and safe return to euglycemia from hypoglycemic and hyperglycemic states, and for managing situations that begin with BGC within the target range, but which can be expected to entail transient hyperglycemia. Embodiments of the invention disclosed herein offer several advantages over the art in how they help a user to manage BGC in situations in which BGC has strayed or will stray outside of the target range. These advantages are delineated in the descriptions and examples below.

SUMMARY

Embodiments of the invention disclosed herein relate to systems and methods for monitoring blood glucose concentration (BGC) levels in a diabetes patient. When monitoring BGC in a diabetes patient it is necessary to establish BGC-based criteria that prompt actions intended to adjust and optimize BGC. Embodiments of the present invention for the first time provide a method whereby a user of a continuous glucose monitor can establish continuously fluctuating upper and lower blood glucose thresholds that, when crossed by the patient's BGC, trigger notifications to the user. The importance of the embodiments of the invention is that they allow the user to manage common fluctuations in BGC due to the short-term effects of food consumption, insulin delivery aberrations, physical activity, emotions, and unforeseen circumstances.

Embodiments of the invention provide for a blood glucose monitoring system comprising a blood glucose notification threshold profile, wherein the threshold profile comprises an upper BGC threshold level and a lower BGC threshold level, and wherein said upper threshold and said lower threshold are programmable to fluctuate continuously over time. Such threshold profiles may be created or designed by a user and/or by a manufacturer of BGC monitoring products, and they may be selected and/or modified by a user and employed by the user as frequently as desired to manage the short-term effects of food consumption, insulin delivery aberrations, physical activity, emotions, and unforeseen circumstances.

Embodiments of the invention also encompass a glucose monitoring system comprising a blood glucose notification threshold profile, wherein the profile comprises an upper BGC threshold level and a lower BGC threshold level, wherein said upper threshold and said lower threshold are programmable to fluctuate continuously over time, and also an alarm to notify a user should the actual monitored BGC stray above said upper threshold or below said lower threshold. In response to said alarm, a user may take action to optimize BGC, and a new blood glucose notification threshold profile may be created, selected and/or modified by the user and employed by the user to continue to manage the short-term effects of food consumption, insulin delivery aberrations, physical activity, emotions, and unforeseen circumstances.

Embodiments of the invention further encompass methods of creating a blood glucose notification threshold profile comprising establishing a mathematical relationship between the upper and lower thresholds of a threshold profile and an expected BGC as a function of time (t).

Embodiments of the invention further encompass methods of establishing an expected BGC as a function of time comprising designating an expected maximum or minimum BGC, a first length of time from the start ($t_0$) to reach said maximum ($t_{max}$) or minimum ($t_{min}$) BGC, and a second length of time from said maximum ($t_{max}$) or minimum ($t_{min}$) BGC to a time when BGC enters a designated target range ($t_{targ}$). Other embodiments of the invention encompassing methods of establishing an expected BGC as a function of time allow for the absence of an expected maximum or minimum, in which case a length of time from the start ($t_0$) to a time ($t_{targ}$) when BGC enters a designated target range is specified. Reflecting these designated values, expected BGC as a function of time and a blood glucose notification threshold profile can be established. Expected BGC as a function of time may be established, for example, by fitting the designated values using a non-linear least squares fit to a segment of a bell-shaped curve whose mathematical form is known in the art.

Embodiments of the invention also contemplate numerous methods with which to program a blood glucose notification threshold profile into a glucose monitoring system. The methods include, but are not limited to drawing a threshold profile, a graph of an expected BGC function, a graph of an upper BGC threshold function, or a graph of a lower BGC threshold function onto a display screen of a continuous glucose monitor; spotting threshold profile points, expected BGC function values, upper BGC threshold function values, or lower BGC threshold function values on a display screen of a continuous glucose monitor and then fitting a function to said points; and using keys to input values of threshold profile points, expected BGC function values, upper BGC threshold function values, or lower BGC threshold function-values into a program that can fit a function to the inputted values.

BRIEF DESCRIPTION OF THE DRAWINGS

Embodiments of the invention may be more completely understood in consideration of the detailed description in connection with the accompanying drawings, in which:

FIGS. 4A and 4B depict a threshold profile established by a user and a BGC level in relation to the threshold profile over time. See Example 4 for details.

FIGS. 10A and 10B depict a threshold profile established by a user and a BGC level in relation to the threshold profile over time. See Example 10 for details.

Figure 1A:
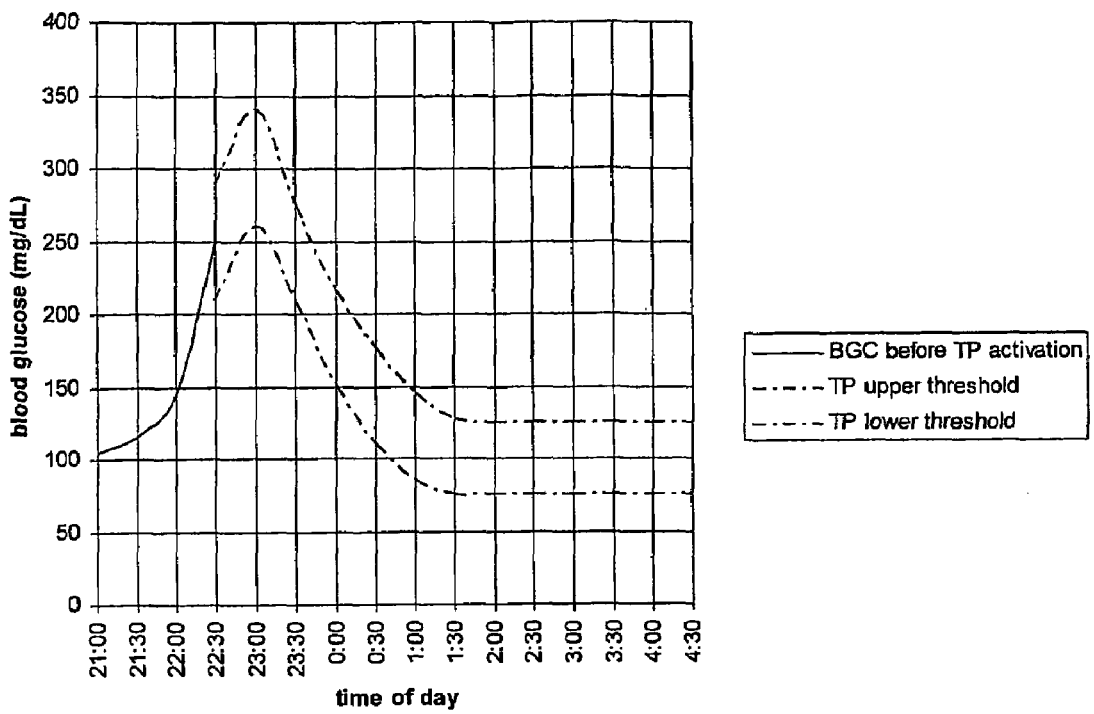
FIGS. 1A and 1B depict a threshold profile established by a user and a BGC level in relation to the threshold profile over time. See Example 1 for details.

While embodiments of the invention are amenable to various modifications and alternative forms, certain specific embodiments are shown by way of example in the drawings and are described in detail below. It should be understood that the intention is not to limit the invention to the particular embodiments described. On the contrary, the intention is to cover all modifications, equivalents, and alternative forms falling within the scope and spirit of the invention as defined by the appended claims.

DETAILED DESCRIPTION OF INVENTION

Embodiments of the invention disclosed herein relate to systems and methods for monitoring blood glucose concentration (BGC) levels in a diabetes patient. Embodiments of the invention provide for a blood glucose notification threshold profile, wherein the profile comprises an upper BGC threshold function and a lower BGC threshold function, and wherein said upper threshold and said lower threshold are programmable to fluctuate continuously over time. Embodiments of the invention further contemplate a glucose monitoring system comprising said blood glucose notification threshold profiles, wherein said threshold profiles may be created or designed by a user and/or by a manufacturer of BGC monitoring products, and said profiles may be selected and/or modified by a user and employed by the user as frequently as desired to manage the short-term effects of food consumption, insulin delivery aberrations, physical activity, emotions, and unforeseen circumstances. Embodiments of the invention further encompass methods of creating and programming blood glucose notification threshold profiles into a glucose monitoring system.

DEFINITIONS

The following are definitions of terms used in this specification.

The term "user", as in "user of a continuous blood glucose monitor", as used herein means any individual who may act upon data or notifications generated by the device being used. Typically, a user is the patient, but the term "user" may also apply to other interested parties, such as adults who care for a child patient. The user may be more than one person, for instance the patient during daytime and the patient's parents during nighttime.

The terms "glucose monitor" and "display", as in "glucose monitor display", as used herein mean devices, either worn by a patient or remote from the patient, that monitor and/or display the patient's blood glucose concentration data and provide notifications to a user. A glucose monitor and/or its display may be combined with other devices such as an insulin pump or a wristwatch. A dedicated remote device, a personal computer, a laptop computer, a palm computer, tablet computer, personal digital assistant, or other digital device may serve as display and user interface devices. The connections between glucose monitors, displays, and other devices may be through wired or wireless connections.

The terms "blood glucose concentration data" and "blood glucose concentration" (BGC), as used herein and as they relate to glucose monitors mean information about blood glucose concentration that is either directly measured by sampling blood or related fluids, such as interstitial fluid, or inferred or calculated by measurement of other parameters that correlate with blood glucose concentration, such as electromagnetic impedance.

The term "continuous" as used herein and as applied to blood glucose monitoring or blood glucose concentration data means frequently enough to avoid missing significant maxima or minima. Continuous blood glucose monitoring may update every few seconds, for example every 1-5 seconds, every 5-15 seconds, every 15-30 seconds, or every 30-60 seconds. Alternatively, continuous blood glucose monitoring may update every few minutes, for example every 1-5 minutes, every 5-15 minutes, or every 15-30 minutes. In this context, the term "continuous" may be synonymous with the term "semi-continuous".

The term "continuous" as used herein and as applied to fluctuating BGC threshold functions, as in the phrase "threshold functions are programmable to fluctuate continuously over time", means that gaps and segments of infinite slope, if any, in a BGC threshold as a function of time are smaller than 30 minutes in the time dimension and smaller than 25 mg/dL in the BGC dimension. In this context, the term "continuous" may be synonymous with the term "semi-continuous".

The term "fluctuate" as used herein and as applied to fluctuating BGC threshold functions, as in the phrase "threshold functions are programmable to fluctuate continuously over time", means to vary, especially irregularly. To "fluctuate continuously over time" means to "change continuously over time" as shown, for example, in FIGS. 1-12.

The term "notification" as used herein means a signal or alert from a blood glucose monitor to a user. The signal or alert may be auditory, visual, tactile, etc. A notification may be an alarm in the sense that it indicates that the monitored BGC is not as expected or is at a level that is reason for concern. Notification may also be confirmation that BGC is as expected or at a desirable level. A blood glucose monitoring system may simultaneously employ several different types of notification signal that may be triggered by different criteria.

The terms "expected range" and "expected blood glucose concentration range" as used herein mean a range of BGC that a user expects at any given time. An expected range is bounded by an upper threshold and a lower threshold. According to embodiments of the present invention, a notification is triggered when monitored BGC exits the expected range by crossing either the upper or lower threshold. Under certain conditions, remaining within the expected range may also trigger a notification. Typically, the user/patient acts to maintain BGC within the target range; however, because circumstances often arise that make maintaining BGC within the target range temporarily impossible, the user/patient may define an expected BGC range, which may differ from the target range, and within which BGC is steered over time to minimize its deviation from the target range.

The term "expected blood glucose concentration" as used herein means a BGC value that a user expects is most likely at any given time. The expected BGC is within the expected BGC range. The expected BGC may be the arithmetic mean, geometric mean, harmonic mean, other average, or other function of the upper or lower BGC threshold functions. An "expected blood glucose concentration function" is a function of expected blood glucose concentration over time, the function comprising specific values at specific times.

The terms "measured blood glucose concentration" and "measured blood glucose concentration function" as used herein refer to blood glucose concentration data obtained from measurements of actual blood glucose concentration data in a user/patient. Such data may be stored in a data store configured to store blood glucose-related data. Measured blood glucose concentration functions comprise specific values at specific times.

The term "notification threshold" as used herein means a BGC value, which may be time-dependent, especially the upper or lower bounds of an expected range. A notification, or alert to a user is triggered when measured, or current, BGC crosses a notification threshold.

The terms "threshold profile" (TP), "blood glucose notification threshold profile" and "blood glucose threshold profile" as used herein mean a pair of functions comprising upper and lower blood glucose notification thresholds as functions of time. The upper and lower BGC notification threshold functions are the upper and lower bounds of an expected BGC range. The upper and lower blood glucose notification threshold functions may be conveniently visualized as graphs, or curves, of glucose concentration versus time.

The term "threshold functions" as used herein refer to the upper and lower BGC threshold functions which comprise a threshold profile. Threshold functions comprise specific values at specific times.

The terms "define" and "defining" as used herein as in "to define a threshold profile" or "defining a threshold function" refer to retrieving, creating, or programming threshold profiles, blood glucose concentration threshold functions, and expected blood glucose concentration functions. A threshold profile, threshold function, or expected BGC function may be created de novo by drawing graphs, spotting points, or entering numeric data. In addition, a threshold profile may be defined by first retrieving blood glucose-related data, such as threshold profiles, upper blood glucose concentration threshold functions, lower blood glucose concentration threshold functions, expected blood glucose concentration functions, or measured blood glucose concentration functions, and then completing the definition of the threshold profile, if necessary, as described herein. The retrieved blood glucose-related data items may optionally be modified as part of the process of defining a threshold profile.

The terms "corresponding" and "corresponding values" as used herein refer to points or values that correspond in time to one another. A threshold profile comprises upper and lower blood glucose concentration notification thresholds as functions of time. The functions further comprise values. When a threshold profile is in use, the current blood glucose concentration value is compared to the upper and lower BGC threshold values that correspond, in the time coordinate, to the current BGC value, which may be either a single BGC value, an average of recent values, and/or a function of recent values such as recent values that have been run through a Kalman filter.

The term "normal range" as used herein means a range of blood glucose concentration that is typical of individuals with normal glucose metabolism. A BGC in the normal range is equivalent to euglycemia, generally more than 65-80 mg/dL and less than 120-140 mg/dL.

The terms "near the normal range" and "near euglycemia" as used herein mean blood glucose concentration that is slightly above or below the normal range, but which is not reason for concern.

The term "target range" as used herein means a range of blood glucose concentration that is recommended for a patient by the patient's healthcare professional. A target range is typically similar to the normal range, but may differ from patient to patient or depend on experience or circumstance. For example, a target range may be higher during a patient's sleeping hours than during his waking hours.

The terms "blood glucose concentration target" and "target" as used herein mean a patient's optimal BGC, as recommended for the patient by the patient's healthcare professional. A target may be the arithmetic mean, geometric mean, or other function of the bounds of the target range.

The term "bolus" as used herein, as a noun as in "insulin bolus", as a verb as in "to bolus insulin", and as an adjective as in "bolus insulin", refers to insulin administered or the act of administering insulin on an ad hoc basis, such as to control BGC after a meal or to decrease an undesirably high BGC. The term is typically applied to the ad hoc subcutaneous infusion of insulin by means of an insulin pump in the context of insulin pump therapy. In multiple daily injection therapy, in which insulin is administered by means of an insulin syringe or insulin pen, the term "bolus insulin" is less frequently used; in this context the term "injection" is more often employed to describe insulin administered subcutaneously on either an ad hoc or other basis. Bolus insulin, when administered, is administered as a supplement to "basal insulin", which is a basal dose of insulin calculated to maintain a steady BGC when BGC is not influenced by a meal or by a significant change from the normal level of physical activity. Basal insulin is employed in both insulin pump and injection therapy. In injection therapy, the basal insulin injected is a longer-acting insulin preparation as compared with the preparation used for ad hoc purposes. In contrast, in insulin pump therapy, the same insulin preparation is used as both the basal and bolus insulin. In insulin pump therapy, bolus insulin is distinguished from basal insulin by the flexibility with which it is used and by the purpose for which it is used—basal insulin is infused in a scheduled fashion to meet the ever-present need for a minimal amount of insulin to control BGC, even in the absence of a meal, while bolus insulin is infused in an ad hoc manner when additional insulin is needed.

The term "computer readable medium" as used herein refers to a digital medium which may be read by a computer, processor, microprocessor or other digital device. Examples of computer readable media include, but are not limited to, CDROM's, CDRW, Random Access Memory (RAM), including Dynamic Random Access Memory (DRAM) and Static Random Access Memory (SRAM), hard disks, such as contained in hard disk drives, floppy disks, digital memory sticks, Digital Video Disks (DVD), and magnetic tape.

The term "data store" as used herein refers to a digital data storage medium capable of being read from and written to. A "data store" may be used to store at least one blood glucose-related data item. Blood glucose-related data items comprise threshold profiles, upper blood glucose concentration threshold functions, lower blood glucose concentration threshold functions, and expected blood glucose concentration functions, as well as measured blood glucose concentration data items. A "data store" may comprise a CDROM, CDRW, Random Access Memory (RAM), including Dynamic Random Access Memory (DRAM) and Static Random Access Memory (SRAM), hard disks, such as contained in hard disk drives, floppy disks, digital memory sticks, Digital Video Disks (DVD), and magnetic tape. Typically a "data store" is either RAM or a disk drive connected, via a wired or wireless connection, to a continuous blood glucose monitor.

The term "numeric input" as used herein, as in the phrase "a device capable of accepting numeric input", means not only input in the form of numbers, but also input that adjusts pre-existing numbers upward or downward, such as by pressing up arrow and down arrow keys.

EMBODIMENTS OF THE INVENTION

Embodiments of the invention comprise continuous blood glucose monitoring systems configured to continuously receive signal data from blood glucose monitoring sensors. Blood glucose monitoring sensors may monitor blood glucose levels directly, or other physiological parameters which are correlated with blood glucose concentration may be monitored. The systems are configured to convert sensor data into current blood glucose concentration values and to compare the BGC values with corresponding threshold profile values. The systems are configured to support continuously fluctuating blood glucose notification threshold profiles. The threshold profiles comprise an upper blood glucose concentration threshold function and a lower blood glucose concentration threshold function, and the functions comprise specific values at specific times. Systems of the invention are configured to compare a current blood glucose concentration value with a corresponding upper blood glucose concentration threshold value and with a corresponding lower blood glucose concentration threshold value. If the current blood glucose concentration value is greater than the corresponding upper blood glucose concentration threshold value or less than the corresponding lower blood glucose concentration threshold value, then the systems are configured to alert a user. The alert may comprise a visual alert, an auditory alert, a tactile alert, or another type of alert. Systems of the invention may also alert users to other events comprising: a predetermined amount of time passing since threshold profile activation, a predetermined time of day occurring, a user maintaining a blood glucose concentration within the threshold profile range for a predetermined amount of time, a blood glucose concentration crossing a static threshold which is independent of a threshold profile, a rate of change of blood glucose concentration exceeding a threshold rate of change, a rate of change of blood glucose concentration falling below a threshold rate of change, a blood glucose concentration percentage rate of change exceeding a threshold percentage rate of change, a blood glucose concentration percentage rate of change falling below a threshold percentage rate of change, a second derivative of blood glucose concentration over time exceeding a threshold second derivative of blood glucose concentration over time, and a second derivative of blood glucose concentration over time falling below a threshold second derivative of blood glucose concentration over time.

Systems of the invention may further comprise a graphic display capable of displaying one or more graphs comprising upper blood glucose concentration threshold functions, lower blood glucose concentration threshold functions, expected blood glucose concentration threshold functions, and measured blood glucose concentration. Graphic displays of systems of the invention may support color wherein a graph of an upper blood glucose concentration threshold function is displayed in a first color, a graph of a lower blood glucose concentration threshold function is displayed in a second color, a graph of an expected blood glucose concentration function is displayed in a third color, and a graph of measured blood glucose concentration is displayed in a fourth color. The colors may be the same, or the colors may be different from one another.

Systems of the invention may comprise a data store configured to store and retrieve blood glucose-related data. For user convenience, data items may be labeled. For example, mnemonic labels may be used to allow users to quickly comprehend the contents of stored data items. Systems of the invention may be configured to allow a user to define blood glucose threshold profiles by using a method comprising one or more of the following steps: the step of retrieving a blood glucose threshold profile from a data store; the step of modifying a blood glucose threshold profile; the step of retrieving an expected blood glucose concentration function from a data store; the step of modifying an expected blood glucose concentration function; the step of retrieving an upper blood glucose concentration threshold function from a data store; the step modifying an upper blood glucose concentration threshold function; the step of retrieving a lower blood glucose concentration threshold function from a data store; and the step of modifying a lower blood glucose concentration threshold function. Systems of the invention may be configured to allow a user to define a blood glucose threshold profile by analyzing recent measured blood glucose concentration data; retrieving at least one blood glucose-related data item, based upon the analysis, from a data store; optionally modifying the at least one blood glucose-related data item; presenting at least one blood glucose related data item to the user; allowing the user to select a blood glucose-related data item; and optionally allowing the user to modify the selected blood glucose-related data item.

Systems of the invention may also be configured to allow a user to define a blood glucose threshold profile by using a method comprising one or more steps including: the step of drawing the graph of an upper blood glucose concentration threshold function using a device capable of accepting graphic input; the step of drawing the graph of a lower blood glucose concentration threshold function using a device capable of accepting graphic input; the step of spotting points defining an upper blood glucose concentration threshold function using a device capable of accepting graphic input; the step of spotting points defining a lower blood glucose concentration threshold function using a device capable of accepting graphic input; the step of entering numeric data defining an upper blood glucose concentration threshold function using a device capable of accepting numeric input; the step of entering numeric data defining a lower blood glucose concentration threshold function using a device capable of accepting numeric input; the step of drawing a graph of an expected blood glucose concentration function using a device capable of accepting graphic input; the step of spotting points defining an expected blood glucose concentration function using a device capable of accepting graphic input; and the step of entering numeric data defining an expected blood glucose concentration function using a device capable of accepting numeric input. The duration of a threshold profile may be from about one hour to about twelve hours.

Embodiments of the invention comprise methods for using continuous blood glucose monitoring systems. Methods of the invention comprise defining a blood glucose notification threshold profile. As discussed in further detail below, threshold profiles comprise an upper blood glucose concentration threshold function and a lower blood glucose concentration threshold function. The upper and lower BGC threshold functions may fluctuate continuously and may form the bounds of an expected blood glucose concentration range for the duration of the threshold profile. A threshold profile may be defined in a number of ways. The upper and lower BGC threshold functions may be defined directly; they may be defined indirectly as functions of an expected BGC function; an upper BGC threshold function may be used to define a lower BGC threshold function, and optionally an expected BGC function; and a lower BGC threshold function may be used to define an upper BGC threshold function, and optionally an expected BGC function.

The upper and lower BGC threshold functions may be defined directly by drawing graphs of the functions using a graphic input device, such as a stylus or computer mouse or trackball or other graphic input device. The upper and lower BGC threshold functions may also be defined by spotting points with the aid of a graphic input device or by inputting numeric values of points; in either case, the system will define the functions by fitting the functions to the input points. The upper and lower BGC threshold functions may also be defined by selecting a preexisting threshold profile from a data store, by modifying a threshold profile, by selecting preexisting upper and lower BGC threshold functions from a data store, by modifying upper and lower BGC threshold functions, or by a combination of any of the aforementioned methods.

A threshold profile may be defined using an expected BGC function, an upper BGC threshold function, or a lower BGC threshold function. For example, a function representing the behavior of expected BGC versus time may be created by drawing a graph of the expected BGC function using a graphic input device, such as a stylus or computer-mouse or trackball or other graphic input device. The expected BGC function may also be defined by spotting points with the aid of a graphic input device or by inputting numeric values of points; in either case, the system will define the function by fitting the function to the points. The expected BGC function may also be defined by selecting a preexisting expected BGC function from a data store, by modifying an expected BGC function, or by a combination of any of the aforementioned methods. Once the expected BGC function has been defined, then the upper and lower BGC threshold functions may be defined, based upon the expected BGC function. For example, the upper and lower BGC threshold functions may be defined to be, respectively, 15% above and 15% below the expected BGC function. As another example, the upper and lower BGC threshold functions may be defined to be, respectively, 25 mg/dL greater and 20 mg/dL lower than the expected BGC function. Similar methods may be used when an upper or lower BGC threshold function is used as a starting function. Once a function has been defined, the remaining two functions may be defined based upon the first defined function. For example, if an upper BGC threshold function has been defined, then the lower BGC threshold function may be defined to be 30% below the upper BGC threshold function, and optionally an expected BGC function may be defined to be 15% below the upper BGC threshold function.

A threshold profile activates at a start time ($t_0$) with its component upper and lower blood glucose notification threshold functions bracketing current BGC, and it typically ends with its component upper and lower BGC threshold functions approximating the bounds of a target range. A threshold profile may also comprise, in its expected BGC function, at least one extreme point. Extreme points, corresponding to either expected BGC maxima or expected BGC minima, occur at times $t_{max}$ or $t_{min}$. Once a threshold profile has been defined, continuous blood glucose monitoring, using the threshold profile, is activated. Blood glucose concentration values are continuously determined and compared to the threshold profile. If the monitored blood glucose concentration value becomes greater than the corresponding upper BGC threshold value or less than the corresponding lower BGC threshold value, the user is alerted.

Embodiments of the invention may comprise a computer readable medium comprising executable processor code configured to monitor continuous blood glucose concentration data, the code comprising: code for receiving data from blood glucose monitoring sensors; code for converting blood glucose sensor data into blood glucose concentration values; code supporting continuously fluctuating blood glucose notification threshold profiles, the threshold profiles comprising an upper blood glucose concentration threshold function and a lower blood glucose concentration threshold function; and the functions comprising specific values at specific times; code for comparing a current blood glucose concentration value with a corresponding upper blood glucose concentration threshold value; code for comparing a current blood glucose concentration value with a corresponding lower blood glucose concentration threshold value; code for alerting a user when the current blood glucose concentration value is greater than the corresponding upper BGC threshold value or less than the corresponding lower BGC threshold value; and code for alerting a user. The alert may comprise a visual alert, an auditory alert, a tactile alert, or another type of alert. The computer readable medium may further comprise code to alert users to other events comprising: a predetermined amount of time passing since threshold profile activation, a predetermined time of day occurring, a user maintaining a blood glucose concentration within the threshold profile range for a predetermined amount of time, a blood glucose concentration crossing a static threshold which is independent of a threshold profile, a rate of change of blood glucose concentration exceeding a threshold rate of change, a rate of change of blood glucose concentration falling below a threshold rate of change, a blood glucose concentration percentage rate of change exceeding a threshold percentage rate of change, a blood glucose concentration percentage rate of change falling below a threshold percentage rate of change, a second derivative of blood glucose concentration over time exceeding a threshold second derivative of blood glucose concentration over time, and a second derivative of blood glucose concentration over time falling below a threshold second derivative of blood glucose concentration over time.

The computer readable medium of the invention may further comprise code supporting a graphic display capable of displaying one or more graphs comprising upper blood glucose concentration threshold functions, lower blood glucose concentration threshold functions, expected blood glucose concentration threshold functions, and measured blood glucose concentration. Code supporting graphic displays may support color wherein a graph of an upper blood glucose concentration threshold function is displayed in a first color, a graph of a lower blood glucose concentration threshold function is displayed in a second color, a graph of an expected blood glucose concentration function is displayed in a third color, and a graph of measured blood glucose concentration is displayed in a fourth color. The colors may be the same, or the colors may be different from one another.

The computer readable medium of the invention may comprise code supporting a data store configured to store and retrieve blood glucose-related data. For user convenience, data items may be labeled. For example, mnemonic labels may be used to allow users to quickly comprehend the contents of stored data items. A computer readable medium of the invention may comprise code configured to allow a user to define blood glucose threshold profiles by using a method comprising one or more of the following steps: the step of retrieving a blood glucose threshold profile from a data store; the step of modifying a blood glucose threshold profile; the step of retrieving an expected blood glucose concentration function from a data store; the step of modifying an expected blood glucose concentration function; the step of retrieving an upper blood glucose concentration threshold function from a data store; the step modifying an upper blood glucose concentration threshold function; the step of retrieving a lower blood glucose concentration threshold function from a data store; and the step of modifying a lower blood glucose concentration threshold function. A computer readable medium of the invention may comprise code configured to allow a user to define a blood glucose threshold profile; the code comprising: code for analyzing recent measured blood glucose concentration data; code for retrieving at least one blood glucose-related data item, based upon the analysis, from a data store; code for optionally modifying the at least one blood glucose-related data item; code for presenting at least one blood glucose related data item to the user; code for allowing the user to select a blood glucose-related data item; and code for optionally allowing the user to modify the selected blood glucose-related data item.

A computer readable medium of the invention may comprise code configured to allow a user to define a blood glucose threshold profile by using a method comprising one or more steps including: the step of drawing the graph of an upper blood glucose concentration threshold function using a device capable of accepting graphic input; the step of drawing the graph of a lower blood glucose concentration threshold function using a device capable of accepting graphic input; the step of spotting points defining an upper blood glucose concentration threshold function using a device capable of accepting graphic input; the step of spotting points defining a lower blood glucose concentration threshold function using a device capable of accepting graphic input; the step of entering numeric data defining an upper blood glucose concentration threshold function using a device capable of accepting numeric input; the step of entering numeric data defining a lower blood glucose concentration threshold function using a device capable of accepting numeric input; the step of drawing a graph of an expected blood glucose concentration function using a device capable of accepting graphic input; the step of spotting points defining an expected blood glucose concentration function using a device capable of accepting graphic input; and the step of entering numeric data defining an expected blood glucose concentration function using a device capable of accepting numeric input. The duration of a threshold profile may be from about one hour to about twelve hours.

Blood Glucose Notification Threshold Profile Characteristics

The following are characteristics of blood glucose notification threshold profiles in general and of an embodiment of the invention disclosed herein:

A blood glucose notification threshold profile is a continuous glucose monitor feature comprising a pairing of an upper blood glucose concentration notification threshold function and a lower blood glucose concentration notification threshold function.

The upper and lower BGC threshold functions of a threshold profile are compared by a blood glucose monitoring system with evolving BGC to determine if and when a notification to a user should occur. This comparison may be made each time a new BGC data point is obtained, for example. Art methods may be employed to determine if the BGC value exceeds the then current upper BGC threshold value or falls below the then current lower BGC threshold value. Notification may depend on either a single BGC value, a set number of recent values, an average of recent values, and/or a function of recent values such as recent values that have been run through a Kalman filter (Diabetes Technology & Therapeutics 2005, volume 7, pp. 15-27).

Blood glucose notification threshold profiles that may be programmed by a user as frequently as desired, and in which the component notification threshold functions may fluctuate continuously over time, are novel, are particularly useful for managing BGC, and are encompassed within preferred embodiments of the present invention. It is noteworthy that both individual upper blood glucose notification threshold functions and individual lower blood glucose notification threshold functions that may be programmed by a user as frequently as desired, and that may fluctuate continuously over time, are also novel and encompassed within embodiments of the present invention whether or not they are paired as components of a threshold profile.

Embodiments of the present invention comprise at least two purposes—to aid a user in managing BGC in situations in which BGC has strayed or will stray outside of the target range and to enhance the user's skill of predicting how BGC will respond to the various factors that affect it. Nothing precludes the use of a threshold profile in situations in which BGC is and is expected to remain within the target range. In such situations, a threshold profile having static upper and lower BGC threshold functions, the static threshold functions being equal to the bounds of the target range, may be appropriate.

In an embodiment of the present invention, a threshold profile is selected, created, designed, modified, and/or otherwise programmed or defined by a user based on the present situation and his experience, expectations, and immediate plans. A threshold profile represents an expected BGC range as a function of time.

In an embodiment of the present invention, a threshold profile begins with the upper and lower BGC threshold functions bracketing the current BGC, and it typically terminates with the upper and lower BGC threshold functions equaling or approximating the bounds of a target range.

In an embodiment of the present invention, a threshold profile has a finite duration, for example one to twelve hours, preferably two to eight hours. Upon expiration of a threshold profile, a continuous glucose monitoring system optionally prompts a user to set a new threshold profile, and if no new threshold profile is set, it optionally triggers the activation of a threshold profile having static upper and lower blood glucose notification threshold functions equaling the bounds of a target range, provided that current BGC is within the target range.

In an embodiment of the present invention, a threshold profile terminates, and a user is optionally prompted to establish a new threshold profile, when BGC exits the expected range, that is, crosses either the upper or lower BGC notification threshold. A user may also optionally choose at any time to terminate an active threshold profile and to begin a new threshold profile.

In an embodiment of the present invention, a threshold profile and/or a function of expected BGC used to construct the threshold profile is displayed graphically along with current, and optionally, recent BGC data. Such graphs span a number of hours that is optionally chosen by a user. Optionally, a user has the ability to scroll the graphical display through time and to save graphs for review by a healthcare professional.

Advantages of Threshold Profiles

Embodiments of the present invention offer several advantages over the art, including the following:

It is well appreciated that simple, static, BGC notification threshold functions by themselves are inadequate, yet the art enhancements meant to address this inadequacy, such as notification thresholds based on the rate of change of BGC and more complex parameters, are not easily visualized and are, therefore, difficult for an average user to routinely modify to accommodate his situation and plans. A graph of BGC as a function of time is a highly visual and informative format in which to display continuous blood glucose concentration data. Likewise, setting and displaying BGC notification thresholds that evolve with time in a graphical format, as embodied in this invention, makes the thresholds highly visual and easy to understand, and therefore, an average user can better benefit from them and routinely modify them to accommodate his situation and plans.

Regardless of whether BGC is normal, high, low, steady, rising slowly, rising rapidly, falling slowly or falling rapidly, in embodiments of the present invention alarms occur only when BGC leaves a time-dependent range that a user chooses based on his expectations and specific plans with his particular circumstances in mind. This aspect of embodiments of the invention is advantageous over the art because it eliminates redundant, excessive, and needlessly annoying alarms and may provide an earlier warning when BGC does not evolve in the anticipated or planned manner.

With art alarm systems, certain types of alarms need to be disabled or ignored in many situations. Embodiments of the present invention provide a means for a user to maintain a fully active alarm system while BGC is managed through any situation. This difference makes it more likely that a user will stay fully engaged in blood glucose control when using embodiments of the present invention.

Employing an embodiment of the present invention, a user plots the course of expected BGC based on his expectations and specific plans with his particular circumstances in mind. The user then receives feedback about whether BGC actually evolves as planned. This encourages the user to enhance his skill of predicting how BGC will respond, over the course of several hours, to the various factors that influence it. Since the prediction/feedback cycle may be tailored to a user's preference in terms of precision, cycle time, and optional game features, embodiments of the invention provide a very flexible tool with which users of all ages and levels of experience and ability may enhance their skills.

With embodiments of the present invention, the focus is on prediction. In this sense, a user interacts with a continuous blood glucose monitor under conditions of hypoglycemia or hyperglycemia in the same manner in which he interacts with it under conditions of euglycemia—he plots the future course of BGC. Thus, embodiments of the invention reinforce the psychologically important notion that it is normal for BGC to occasionally stray, and at the same time it supports the goal of maximizing time spent in euglycemia.

Programming/Defining Threshold Profiles

There are a number of methods by which a user may program threshold profiles. A user may create a threshold profile de novo on a display screen of a continuous glucose monitor. A user may select a threshold profile from a set of profiles offered by a continuous glucose monitor. A user may first select an approximation of a desired threshold profile from a set of profiles offered by a continuous glucose monitor and then modify the chosen threshold profile to his specifications. These methods are discussed in greater detail below.

Alternatively, a user may create a graph of expected BGC as a function of time de novo on a display screen of a continuous glucose monitor, select a graph of the expected BGC function from a set offered by a continuous glucose monitor, or select an approximation of a desired graph of the expected BGC function from a set offered by a continuous glucose monitor and then modify it. In any case, the graph of the expected BGC function would begin with the then current actual BGC. Next, a user may apply standard methods to establish a mathematical relationship between the upper and lower BGC threshold functions of a threshold profile and the expected BGC function. The relationship between the threshold functions and expected BGC function may be a modifiable default relationship. For example, the upper and lower BGC threshold functions may, for the entire threshold profile, be 15% greater than and 15% less than the expected BGC, respectively, or 25 mg/dL greater than and 20 mg/dL less than the expected BGC, respectively.

Sources of Threshold Profiles and Expected BGC Functions from which to Select

Threshold profiles and the expected BGC functions that are offered by a continuous glucose monitor may have any of several origins. They may be loaded onto a continuous glucose monitor prior to its distribution by a manufacturer. As such, they may be incompletely defined and then completely defined by the device or user to conform with real time BGC data prior to selection (see below). They may be created de novo or by modification of pre-existing versions on a user's personal computer, and then loaded onto a continuous glucose monitor. They may be designed remotely by a healthcare provider, another user, or a manufacturer of a continuous glucose monitor, then transferred to a user's personal computer via the internet or other wired or wireless network, a CD, or another computer readable storage medium, and then, after optional user modification, loaded onto a continuous glucose monitor. They may be historical functions of actual BGC vs time. They may be previously used threshold profiles or functions of expected BGC that were saved. They may be threshold profiles or functions of expected BGC that were previously created de novo on a display screen of a continuous glucose monitor and saved for future use.

Creation of Threshold Profiles and Expected BGC Functions

Threshold profiles and expected BGC functions may be created de novo employing known methods for drawing lines on a display screen. A user may draw upper and lower notification threshold functions or a function of expected BGC versus time as lines directly on a display screen of a continuous glucose monitor with a stylus or fingernail if the continuous glucose monitor is equipped with a type of display screen that may be drawn upon, for example, similar to that of a PDA device in notepad mode. In the absence of this type of display screen, or for instance if a standard personal computer is functioning as the continuous glucose monitor's user interface, a mouse or touch pad or trackball may be used to draw threshold or expected BGC functions. The display screen may have a graphing grid background against which to draw. The display screen may show current, and optionally, recent BGC data while threshold or expected BGC functions are being drawn. Button presses, a touch screen menu, or operation of a mouse or touch pad or trackball may allow a user to begin drawing, indicate completion of drawing, and accept or reject the drawn threshold functions or expected BGC function. A zoom capability and/or a curve/function fitting algorithm may optionally be utilized to facilitate the drawing process. Valid threshold profiles may begin by bracketing the current BGC and valid functions of expected BGC may begin with the current BGC.

Alternatively, threshold profiles and functions of expected BGC may be drawn on a display screen with a stylus, fingernail, mouse or touchpad or trackball by first spotting points, rather than drawing lines, and then employing a line smoothing/curve fitting algorithm to fully define the functions. In addition, threshold profiles and expected BGC functions may be created de novo by inputting the values of points into a software program that can fit a function from those values, such as Microsoft Excel. Such values may be input using standard methods, for example, by typing point coordinates or using up/down and optionally left/right arrows and an enter button function.

Parameterization and Selection of Threshold Profiles and Expected BGC Functions

When a user selects a threshold profile or an expected BGC function from a set offered by a continuous glucose monitor, the items most conveniently accessed, or suggested by the device, may be tailored to the situation. The device may tailor the selection based on the current BGC and its current rate of change. For example, if current BGC is above the target range and rising, then the device may restrict the choices offered to those with a predicted maximum above the current BGC. Also, each choice may be automatically modified by the device such that the upper and lower BGC threshold functions bracket the current BGC or the expected BGC function begins with the current BGC and such that the initial rate of change of expected BGC matches the actual rate of current BGC change. The choices may be displayed one at a time on the device, or they may be displayed simultaneously as a matrix. Up/down arrow, left/right arrow, and enter button presses, a touch screen menu, operation of a mouse or touch pad, or other standard features may allow a user to navigate or scroll among the choices and make his selection. The device may provide a variety of threshold profiles or expected BGC functions that vary with respect to easily understood, fundamental parameters, such as an expected maximum or minimum BGC (defaulting to the current BGC if no maximum or minimum that differs from the current BGC is expected), a length of time from the start ($t_o$) to the expected maximum ($t_{max}$) or minimum ($t_{min}$) BGC (zero if no maximum or minimum that differs from the current BGC is expected), and a length of time from the maximum ($t_{max}$) or minimum ($t_{min}$) (or the present if no maximum or minimum that differs from the current BGC is expected) to a time ($t_{targ}$) at which expected BGC enters a target range, assuming that the expected maximum or minimum (or the current BGC if no maximum or minimum that differs from the current BGC is expected) is outside of the target range. For cases in which expected BGC crosses from outside to inside of a target range, the device's software may provide for expected BGC to approach a BGC target asymptotically or for expected BGC to superimpose upon a BGC target within a finite amount of time. If neither current BGC nor an expected maximum or minimum are outside of a target range, a user may set the upper and lower BGC threshold functions of a threshold profile to remain constant and to equal or approximate the upper and lower bounds of a target range as per the art.

A function of expected BGC over time (t) may be established from the fundamental parameters noted above by, for example, using a non-linear least squares fit to a segment of a bell-shaped curve whose mathematical form is known in the art. To accomplish this fit, a segment of one bell-shaped curve may be used for the portion of the expected BGC function before an expected maximum or minimum, and a segment of a different bell-shaped curve may be used for the portion of the expected BGC function after the expected maximum or minimum. The following is an example of a mathematical form that the portion of an expected BGC function after an expected maximum may take:

$$(\text{expected BGC} - \text{target BGC}) \div (\text{maximum BGC} - \text{target BGC}) = b\hat{\ }((k[t-t_{max}])\hat{\ }p)$$

In this example, the symbol "^" indicates the raising of the term to its left to the exponential power of the term to its right. That is, the term "$k[t-t_{max}]$" is raised to the power of "p", and "b" is in turn raised to the power of "$((k[t-t_{max}])\hat{\ }p)$". The term "$t-t_{max}$" indicates an amount of time after $t_{max}$ at which expected BGC at time t is calculated. The terms "b", "p", and "k" have the following meanings and constraints: The term "b" is a dimensionless base between 0 and 1, preferably between 0.1 and 0.9; the term "p" is a dimensionless exponent greater than 1 and preferably less than 5, for example 1.5 or 2.0; and the term "k" is a constant having the dimensions of reciprocal time, for example $0.5\ h^{-1}$ or $1.3\ h^{-1}$. The terms "b", "p", and "k" may be chosen such that on an expected time scale expected BGC declines from the expected maximum BGC to within the target range wherein it asymptotically approaches the target BGC. As will be appreciated by those skilled in the art, variations on this mathematical form may also be employed to fit the portion of an expected BGC function before an expected maximum, as well as the various portions of expected BGC functions having other forms, such as those entailing an expected minimum. However, this type of mathematical form is but one of many possible ways to model the behavior or expected BGC over time. Other mathematical forms known in the art are possible.

In order to limit the choices of threshold profiles and expected BGC functions to those most reasonable, the device may treat the parameters which vary among the choices as partially interdependent. For example, if when setting a new threshold profile the current BGC is above a target range and rising, a user will most likely take corrective action, such as insulin administration, to reverse the rising trend and return BGC to the target range. The aggressiveness of corrective action, i.e. the amount of insulin administered, can reasonably be reflected in each of the expected maximum BGC value, the time from the present to the expected maximum, and the time from the expected maximum to entry into the target range. The more insulin administered, the lower the expected maximum BGC value, the sooner it will occur, and the shorter the time interval from the maximum to entry into the target range. Thus, the aggressiveness of anticipated or recently executed corrective action can be employed as a meaningful parameter that impacts, in ways that may correlate, each of these fundamental parameters that may describe a threshold profile or function of expected BGC. Recognition of this fact provides a means for a blood glucose monitoring system to focus an initially offered set of threshold profiles and expected BGC function choices. For example, if when setting a new threshold profile, the current BGC is 30 mg/dL above the target range and rising at a rate of 100 mg/dL per hour, the initial set of choices offered by the device might include a 3 by 3, or more generally an m by n, matrix of expected BGC functions, each tailored to the situation of the current BGC being 30 mg/dL above the target range and rising at a rate of 100 mg/dL per hour. One dimension of the matrix, for example the different rows of the matrix, may reflect variation in the aggressiveness of corrective action. In a first row, a highly aggressive corrective action may correspond to an expected maximum BGC only 40 mg/dL above the current BGC, and that may be correlated with a time from the present to the maximum of only 30 minutes. In a second row, a moderately aggressive corrective action may correspond to an expected maximum 80 mg/dL above the current BGC, and that may be correlated with a time from the present to the maximum of 60 minutes. In a third row, a weakly aggressive corrective action may correspond to an expected maximum 120 mg/dL above the current BGC, and that may be correlated with a time from the present to the expected maximum of 90 min. The second dimension, for example the different columns of the matrix, may vary the ratio of (a) the length of the time from the expected maximum until entry into the target range to (b) the time from the present to the expected maximum. In a first column, each time from the expected maximum to entry into the target range may equal the time from the present to the expected maximum. In a second column, the former may be 1.5 times the latter, and in a third column the former may be 2 times the latter. As noted above, this example 3 by 3 matrix of expected BGC functions has been tailored to the situation of current BGC being 30 mg/dL above the target range and rising at a rate of 100 mg/dL per hour. Other situations, in which current BGC exceeds the target range by other amounts and in which current BGC is rising at other rates, may prompt other sets of expected BGC function choices. Similarly, in situations in which a falling BGC suggests that corrective action should be taken, the device may offer matrices of expected BGC functions that reflect variation in the aggressiveness of carbohydrate consumption as a corrective action that impacts, in ways that may correlate, each of the fundamental parameters: a minimum BGC, a time from the present to the minimum BGC, and a time from the minimum BGC until entry into a target range.

In order to simplify the representation of a threshold profile or expected BGC function when displayed for selection by a user, the device may optionally represent them by non-smoothed line graphs with key points, such as maxima, minima, and target range entry points highlighted, or it may represent them as a list of the easily understood parameters, such as expected maximum BGC, time from the present to the expected maximum, and time from expected the maximum to target range entry, or it may represent them as icons indicating a parameter, such as level of aggressiveness of corrective action, or it may represent them with labels applied to them by a user to indicate a situation in which they are useful, such as "Chinese food" or "forgot to bolus".

Modification of Threshold Profiles and Expected BGC Functions

User modification of threshold profiles and expected BGC functions, either on a continuous glucose monitor or on a personal computer, may be performed in several ways and may involve multiple steps, including, but not limited to those described in this specification. One step is to ensure that the upper and lower BGC threshold functions of a threshold profile bracket the current BGC or that an expected BGC function begins with the current BGC. This step may be performed by shifting the entire upper and lower BGC threshold functions of a threshold profile or an entire expected BGC function to higher or lower values by a constant amount. Alternatively, this step may be performed by increasing or decreasing the values of all points on a threshold profile or an expected BGC function by a constant multiplication factor. Additionally, this step may be performed by proportionally expanding or contracting the difference between all points on an expected BGC function and a BGC target, which entails multiplication of that difference by the ratio of (a) the difference between the BGC target and the current BGC to (b) the difference between the BGC target and the point on the expected BGC function that corresponds in time to the current BGC. Other standard methods to perform this step may also be employed.

Another step that may be taken to modify threshold profiles and expected BGC functions is to fit the initial rate of change of an expected BGC function to an actual rate of change of current BGC. This step may be performed by proportional compression or expansion along the time axis while holding the initial point constant. Other standard methods to perform this step may also be employed.

Both of the two steps described above, ensuring that the upper and lower BGC threshold functions of a threshold profile bracket the current BGC or that an expected BGC function begins with the current BGC, and fitting the initial rate of change of an expected BGC function to an actual rate of change of current BGC, may be performed automatically by the device on all members of a set of threshold profiles or expected BGC functions offered by a continuous glucose monitor for selection by a user.

Another step that may be taken to modify threshold profiles and expected BGC functions is to extend them at their final values for additional time or to truncate them at an earlier time.

Another step that may be taken to modify threshold profiles and expected BGC functions is to adjust the fundamental parameters of an expected BGC function, such as an expected BGC maximum or minimum value, a time from the start ($t_0$) to the expected maximum ($t_{max}$) or minimum ($t_{min}$), and a time from the expected maximum or minimum to entry into a target range ($t_{targ}$). Adjustment of these parameters may be made by up/down arrow, left/right arrow, and enter button presses, with a touch screen menu, by operation of a mouse or touch pad, or with other standard features. A mouse or touch pad may allow a user to select and drag points on a graph. A function fitting algorithm may be used to re-smooth the function after modification. Another parameter that that may be adjusted to modify threshold profiles and expected BGC functions is a parameter reflecting the aggressiveness of a corrective action. As described above, when a corrective action is taken to correct an abnormally high and rising BGC, the more aggressive the corrective action, which typically is insulin administration, the lower the expected maximum BGC value, the sooner it will occur, and the shorter the time interval from the maximum to entry into the target range. When a corrective action is taken to correct an abnormally low and falling BGC, the more aggressive the corrective action, which typically is consumption of carbohydrate, the higher the expected minimum BGC value, the sooner it will occur, and the shorter the time interval from the minimum to entry into the target range. The responsiveness of each of the expected maximum or minimum BGC values, the length of time to the expected maximum or minimum, and the length of time from the maximum or minimum to the time at which BGC enters the target range, to the aggressiveness of corrective action, may be adjusted by a user based on experience and may be set to modifiable default values by either the user or the device manufacturer.

Display of Threshold Profiles and Graphs of Expected BGC Functions

Once a threshold profile is programmed and activated, it may be displayed graphically along with current, and optionally, recent BGC data. A graph of an expected BGC function used to construct the threshold profile may be displayed in addition to, or instead of, the threshold profile itself. The bounds of a target range may also be displayed. Different colors may optionally be employed in the display screen for upper and lower threshold lines, bounds of a target range, a past actual BGC line up to the start of the active threshold profile, an actual BGC line from the start of the threshold profile to the present, and an expected BGC line from the start to the end of the threshold profile. Additionally, background color may vary in different areas of a displayed graph, for example, green between the upper and lower threshold lines and red outside of them. The leading end of an actual BGC line may be marked by a flashing point or a small icon, such as an airplane, car, or train that may be consistent with the concepts of a blood glucose control game.

Notifications Based on Threshold Profiles

The relationship between evolving BGC and the upper and lower BGC threshold functions of a threshold profile is the basis for notifications to a user. Notifications may be auditory, visual, tactile, etc., as described in the art. One type of notification is to generate an alarm to alert a user when a current BGC is greater than a corresponding upper BGC threshold value, or when a current BGC is less than a corresponding lower BGC threshold value. An alarm often may not indicate hypoglycemia or hyperglycemia per se, but rather that the evolution of BGC is different from what the user expected and/or intended. Depending on BGC at the time of threshold programming and the user's expectations and plans, an alarm may signal, for example, current hypoglycemia or hyperglycemia, impending hypoglycemia or hyperglycemia, or that preexisting hypoglycemia or hyperglycemia is not being resolved as quickly as expected and/or intended. Another optional type of notification signals that BGC remains between the upper or lower threshold of the threshold profile. This type of notification confirms that BGC is as a user expected and/or intended for that point in time.

Games Based on Threshold Profiles

Because the purpose of embodiments of the invention is not only to aid a user in managing situations in which BGC has strayed or will stray outside of a target range, but also to enhance the user's skill of predicting how BGC will respond to the various factors that affect it, notifications provided on the basis of the relationship between evolving BGC and the upper and lower BGC threshold functions of a threshold profile may optionally be features of an educational game function. Such a game may, for example, award points to a user depending on the length of time that BGC remains between the upper and lower BGC threshold values of a threshold profile and on the level of difficulty as determined by the size of the spread between the upper and lower BGC threshold functions. As part of a game function, notification may be provided each time a point is awarded to confirm the accuracy of a user's prediction of BGC evolution and to provide positive reinforcement. Both the notification type and features of the display may be adjustable in general and in particular to be consistent with a game function. The display may incorporate a scoreboard to indicate points earned. The leading end of the actual BGC line may be marked by a small icon, such as an airplane, car, or train that may be consistent with the concepts of a game, for example, one in which a user "drives a train" representing BGC. Notifications may include, for example, a train whistle sound for each point earned by maintaining BGC between the upper and lower BGC threshold functions, and a crash sound when the upper or lower threshold is crossed.

Conditional Notifications not Contingent Upon Threshold Profiles

To assist a user in managing BGC in the desired manner, other conditional notifications that are not contingent upon the relationship between evolving BGC and a threshold profile may be employed along with those that are contingent upon the relationship between evolving BGC and a threshold profile. These optional, conditional notifications include reminders that are triggered at a specific time and alerts that are triggered by a current BGC crossing a static threshold which is independent of a threshold profile. For example, a user may set a time reminder or a BGC alert to prompt the consumption of a snack that was planned when a threshold profile was programmed and which is necessary to maintain BGC between the upper and lower thresholds of the threshold profile. Such conditional reminders and alerts may be set at any time relative to the programming of a threshold profile.

EXAMPLES

Examples 1 through 12 are prospective examples that illustrate situations that commonly result in BGC outside of the target range and how threshold profiles may be programmed and used in these situations. The purpose of these examples is to provide some understanding of the scope of embodiments of the invention without implying any limits. Many additional permutations of the various aspects of these examples are possible, as will be obvious to those familiar with intensive blood glucose management. Examples 13 and 14 offer example, high level, programming schemes of actions that may be taken by a continuous glucose monitoring system in embodiments of the invention.

Example 1

Figure 1B:
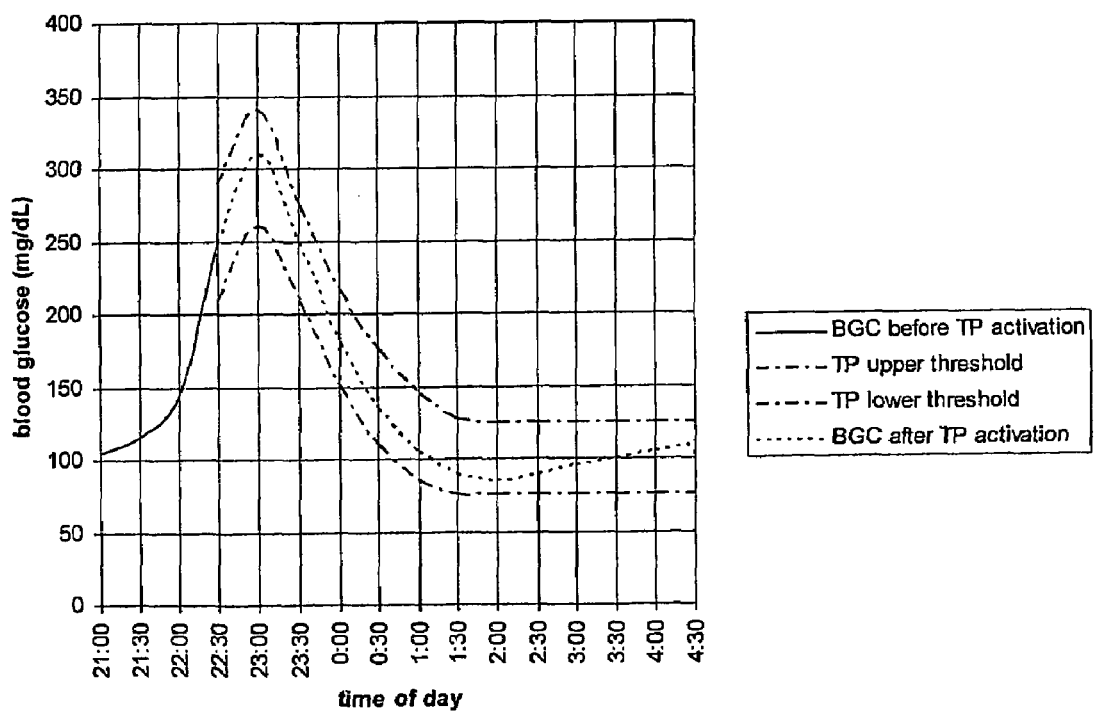

Nicole manages her diabetes with an insulin pump and a continuous glucose monitor that, through a wireless connection, can employ her personal computer as the user interface. One night at home, just after a late dinner, her BGC unexpectedly rises rapidly. Nicole determines that her insulin infusion site has deteriorated, and by the time she changes her infusion set, her BGC is high and still rising. At 22:30, she views the evolution of her BGC on her personal computer, and with the mouse, she draws the upper and lower BGC threshold functions of a threshold profile (TP) based on her expectation that the insulin she has just bolused will take some time to reverse the rise of her BGC and still more time to return it to her target range (FIG. 1A). Because Nicole plans to go to sleep soon, she programs an alarm to ring loudly if her BGC crosses either threshold, but upon expiration of the threshold profile in six hours no sound will signal the default to a threshold profile with upper and lower BGC threshold functions matching the bounds of her target range (125 mg/dL and 75 mg/dL, respectively). Nicole goes to sleep and her BGC evolves approximately as planned (FIG. 1B).

Example 2

Figure 2A:
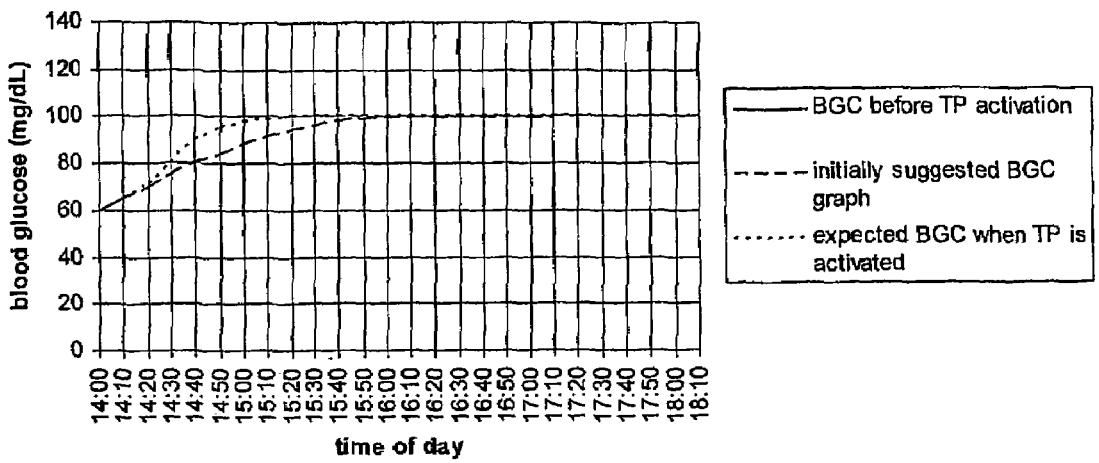
FIGS. 2A and 2B depict a threshold profile established by a user and a BGC lever in relation to the threshold profile over time. See Example 2 for details.
Figure 2B:
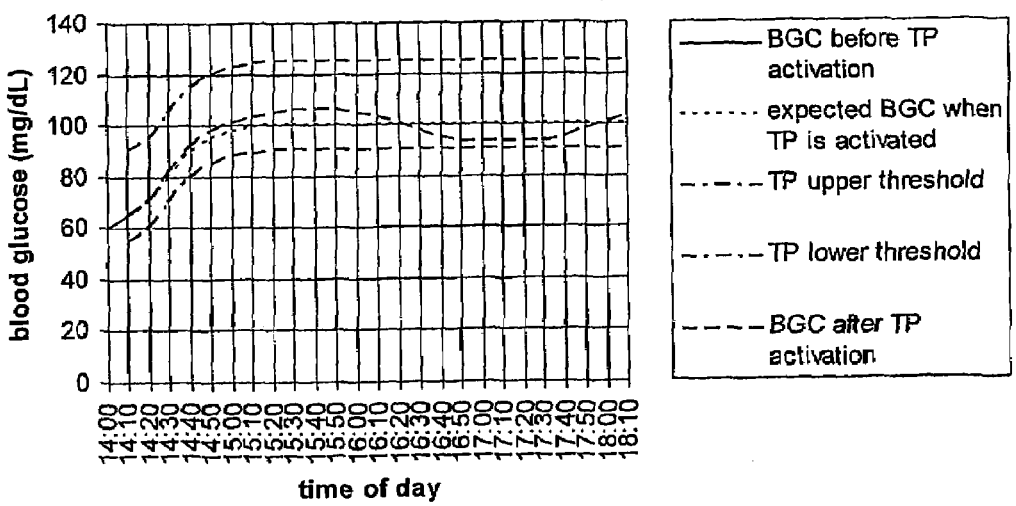

Lindsey manages her diabetes with an insulin pump and a continuous glucose monitor that share the same user interface component. Lindsey removes her pump/monitor to play a soccer game after lunch, figuring that exercise will approximately offset the missing insulin. After the game, at 14:00, when Lindsey reconnects her pump/monitor, her BGC is 60 mg/dL, which is below her usual target range of 80-120 mg/dL, but it is rising at a rate of about 0.5 mg/dL per minute. Lindsey has a snack, boluses insulin, and at 14:10 she accesses a set of graphs of expected BGC functions suggested by her pump/monitor, which has already matched the functions in this set to her current BGC and its rate of change. Lindsey picks one function, but she feels that her snack will increase her BGC more rapidly than indicated by the function she has chosen, so she uses the buttons on her pump/monitor to select the function point at which her expected BGC crosses into her target range, and she moves that point to an earlier time. Also, since the function she has chosen projects only three hours, she extends it another hour so that it lasts until dinner time (FIG. 2A). Lindsey then programs upper and lower BGC threshold functions that are 25 mg/dL higher and 10 mg/dL lower than her expected BGC, respectively. She leaves her notification system in the default, auditory alarm-only mode that will signal if her BGC crosses either threshold. Lindsey's BGC rises about as rapidly as she expected and remains within the bounds she has chosen (FIG. 2B).

Example 3

Figure 3A:
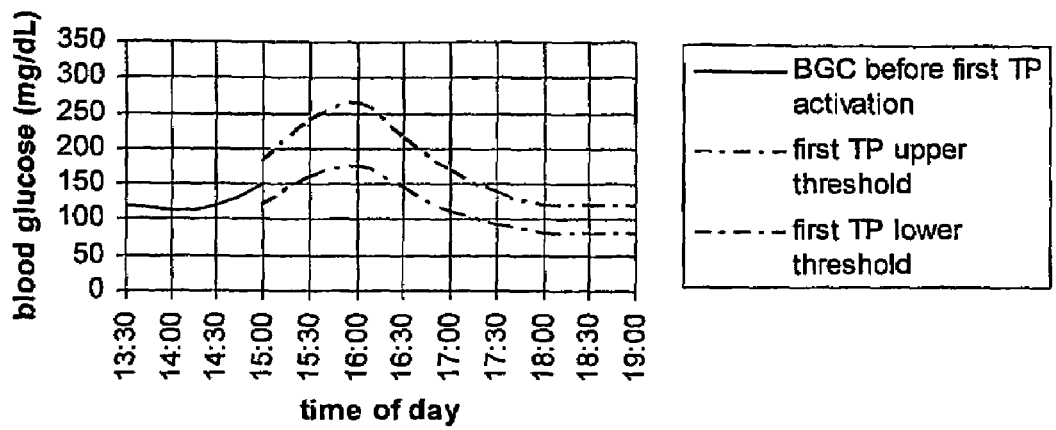
FIGS. 3A and 3B depict a threshold profile established by a user and a BGC level in relation to the threshold profile over time. See Example 3 for details.
Figure 3B:
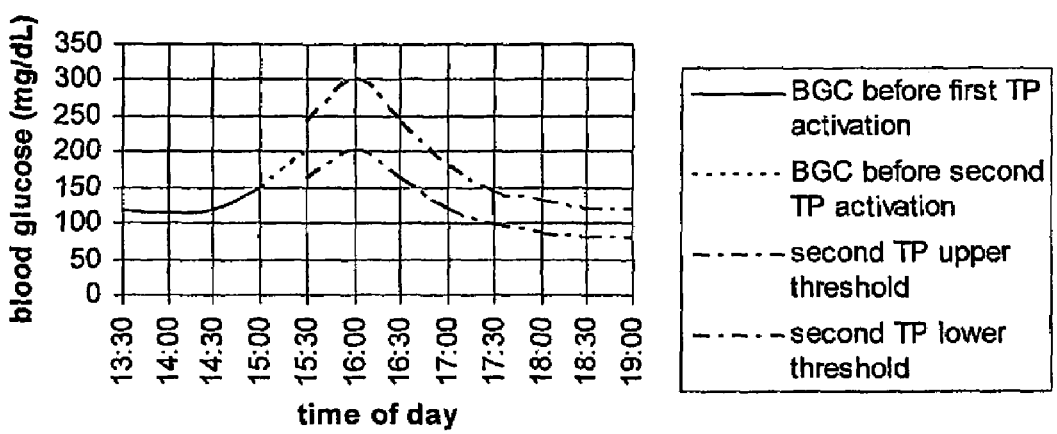

Neil's toddler manages his diabetes with an insulin pump, a continuous glucose monitor, and his father's help. Neil carries a wireless auxiliary device that allows him to interface with his son's glucose monitor. Because his son is an unpredictable eater, Neil often waits until after his son has eaten most of his meal before he asks him to bolus insulin for it. Neil uses this strategy at a pool party, and as often happens, his son's BGC is high and rising by the time he receives insulin to cover the food. At 15:00 Neil uses a stylus to draw the upper and lower BGC threshold functions of a threshold profile lasting four hours on his wireless auxiliary device. The threshold profile predicts a maximum BGC of about 220 mg/dL in 60 minutes and then a decline into the target range (75-125 mg/dL) (FIG. 3A). Neil programs a pleasant chime and green flash of color for every quarter hour that his son's BGC remains between the thresholds that he has drawn, and he chooses a fire alarm sound and a red flash to occur if either of the thresholds is crossed. Neil places the device on a table and has a swim. About 20 minutes later, Neil's son politely requests potato chips. Neil gives his son permission, watches his son eat the chips, estimates how many were eaten, asks his son to bolus more insulin, cancels the active threshold profile, and programs a new one with the same notification options, but which anticipates a higher maximum BGC level (FIG. 3B).

Example 4

Jason, an avid gamer, manages his recently diagnosed diabetes with insulin injections and a continuous glucose monitor with game features. Jason injects his insulin, and after a short time he eats an after-school snack. On his hand-held device Jason sees that his BGC, still in his target range (70-

130 mg/dL), is starting to rise and correctly concludes that it will exceed the upper threshold that is active. He terminates the active threshold profile, and at 15:30 he programs a new one using a stylus to spot the points of a new expected BGC function graph. A function fitting algorithm connects the points with a smooth line. The function peaks at 150 mg/dL, then declines toward his target range. Jason then sets upper and lower thresholds to 30 mg/dL above and below the expected BGC, respectively, and activates the threshold profile (FIG. 4A). As part of the game feature, with the thresholds 60 mg/dL apart, Jason is awarded one point if his BGC remains between the thresholds for ten minutes. He receives two more points if his BGC remains between the thresholds until twenty minutes have elapsed. He earns three more points if his BGC remains between the thresholds until thirty minutes have elapsed, and so on. Jason's threshold profile predicted that his BGC would peak and then begin a decline toward his target range about sixty minutes after it became active. However, when his BGC continued to rise and exceeded his upper threshold after about fifty minutes, Jason's monitor/game device produced a sad, moaning sound, indicating that he would have to start over (FIG. 4B). He had earned fifteen points and was about to receive six more, but now he would again have to start earning them one at a time. Jason would also now have to decide whether or not to inject more insulin and think about how his BGC will behave before programming another threshold profile.

Example 5

Figure 5A:
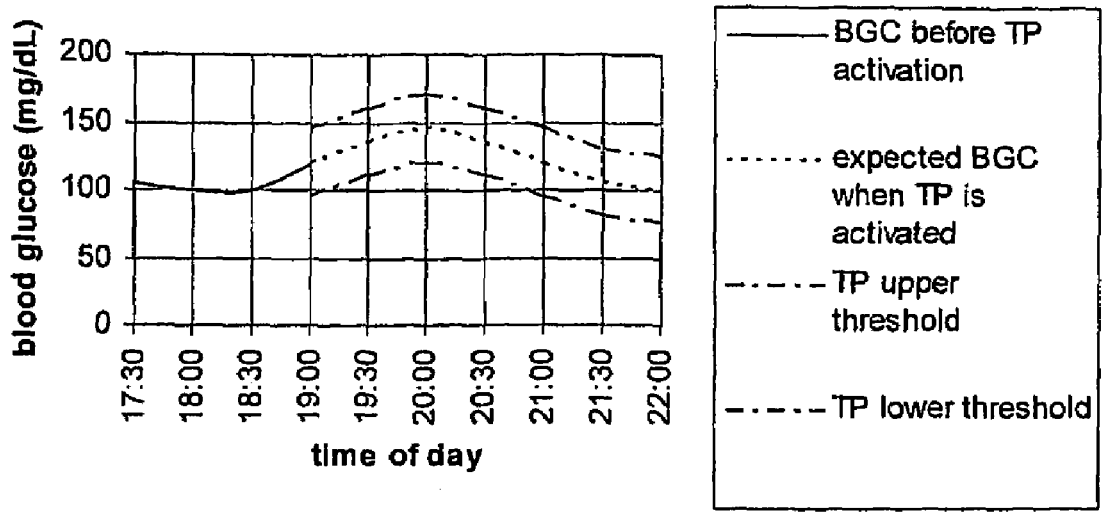
FIGS. 5A and 5B depict a threshold profile established by a user and a BGC level in relation to the threshold profile over time. See Example 5 for details.
Figure 5B:
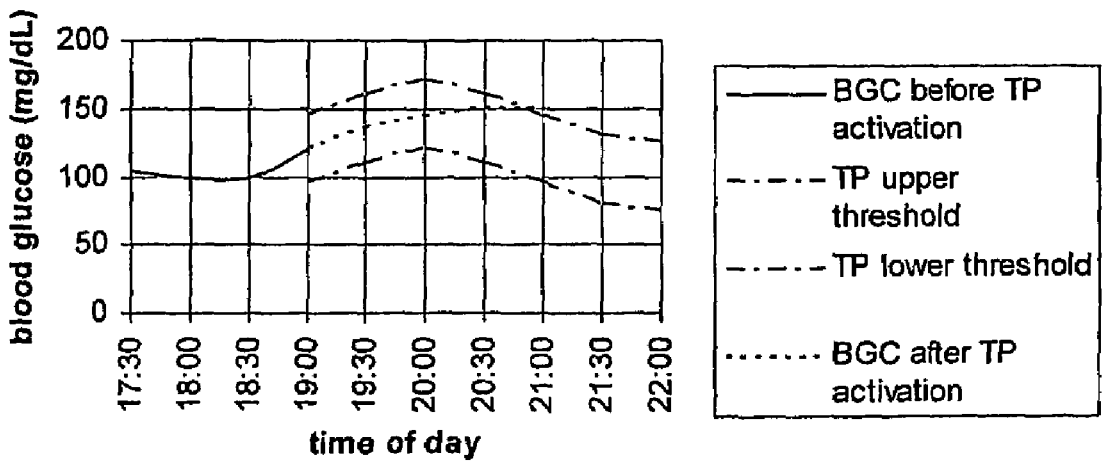

Isaac manages his diabetes with an insulin pump and a continuous glucose monitor, one in each front pocket of his pants. He goes to a movie and buys popcorn, a food that he does not normally eat. Isaac's guess about how many grams of carbohydrates are in his portion of popcorn is incorrect. Even though he has bolused insulin well in advance of eating the popcorn, he sees his BGC rising. Although it is still in his target range (75-125 mg/dL), Isaac can predict that he needs more insulin. Isaac boluses a little more insulin, and at 19:00 he programs a new threshold profile by inputting points of his new expected BGC function using up/down and left/right arrows and an enter button function. The function predicts that his BGC will peak a little above his target range and then decline and stabilize within his target range. Isaac sets his thresholds at 25 mg/dL above and below his expected BGC (FIG. 5A). Because he is in a movie theater, Isaac programs his device to vibrate if his BGC crosses either of the new thresholds. When his BGC crosses the upper threshold by remaining high and steady (FIG. 5B), Isaac's device vibrates. He then boluses more insulin and programs a new threshold profile.

Example 6

Figure 6A:
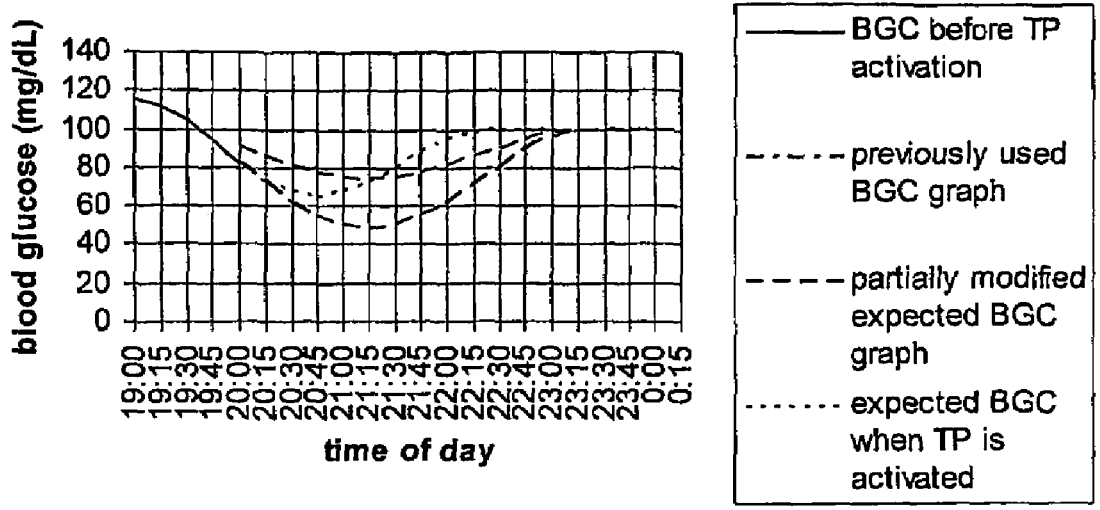
FIGS. 6A and 6B depict a threshold profile established by a user and a BGC level in relation to the threshold profile over time. See Example 6 for details.
Figure 6B:
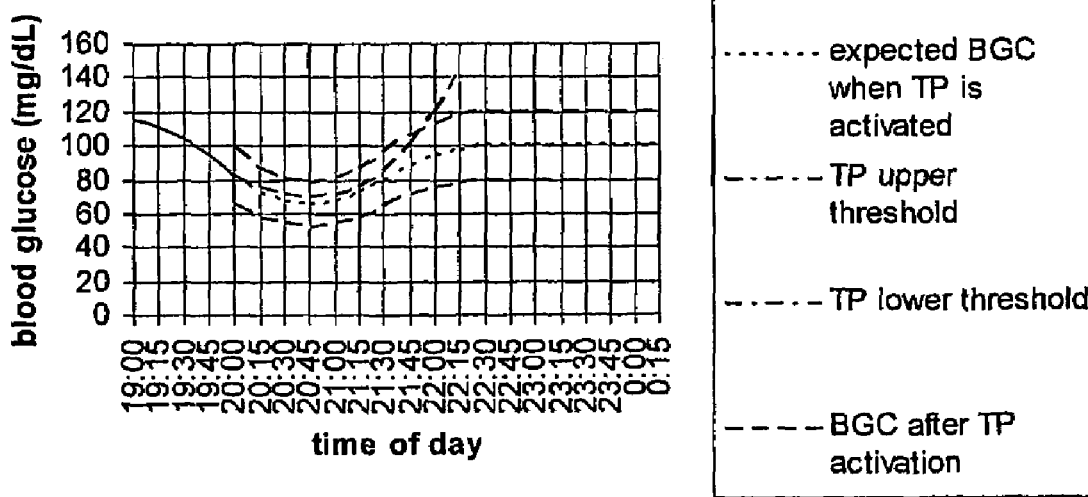

Kryssy manages her diabetes with an insulin pump and a continuous glucose monitor that, through a wireless connection, can employ her personal computer as the user interface. She has dinner at a schoolmate's house where a casserole is the main dish. Kryssy overestimates the carbohydrate content of the casserole. By the time she returns home at 20:00, her BGC is still within her target range (80-120 mg/dL), but it is falling rapidly enough to predict impending hypoglycemia. Kryssy eats a muffin while she programs a threshold profile on her personal computer. She selects a previously used function of expected BGC and matches it to her current BGC by proportionally expanding the difference between all points on the previously used function and her BGC target (100 mg/dL). This step coincidentally also matches the new function to her current BGC rate of change. She then uses the mouse to raise the minimum BGC point and shorten the time until expected BGC re-enters her target range (FIG. 6A). Finally, she sets the thresholds at 20% above and below the expected BGC function, programs an alarm to ring if one of the new thresholds is crossed, and activates the new threshold profile. Because the muffin that Kryssy ate overcompensated for her underestimation of the casserole's carbohydrate content, her BGC trend reverses more rapidly than expected and her upper threshold is exceeded (FIG. 6B). Kryssy's personal computer alarms and alerts her to consider her next action and how it will affect her BGC over the next few hours.

Example 7

Figure 7A:
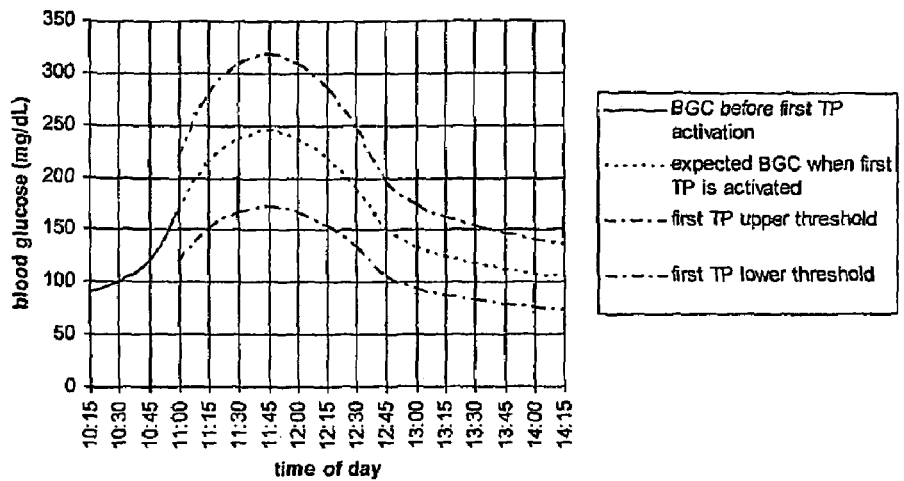
FIGS. 7A, 7B, and 7C depict a threshold profile established by a user and a BGC level in relation to the threshold profile over time. See Example 7 for details.
Figure 7B:
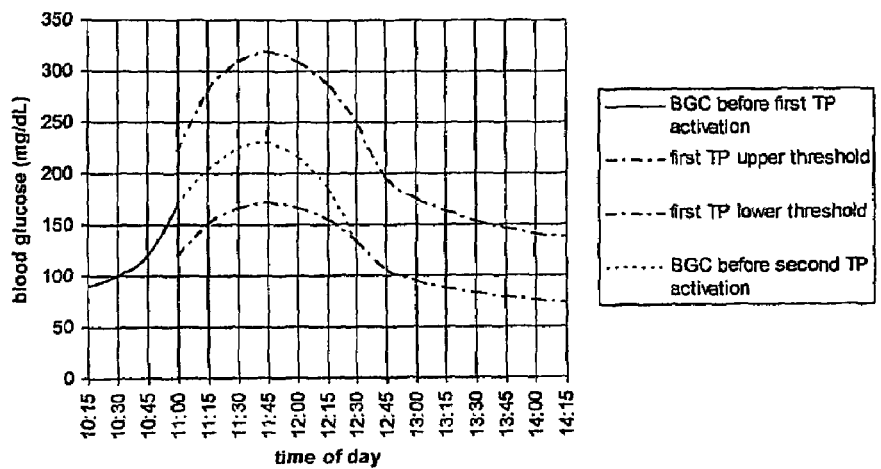
Figure 7C:
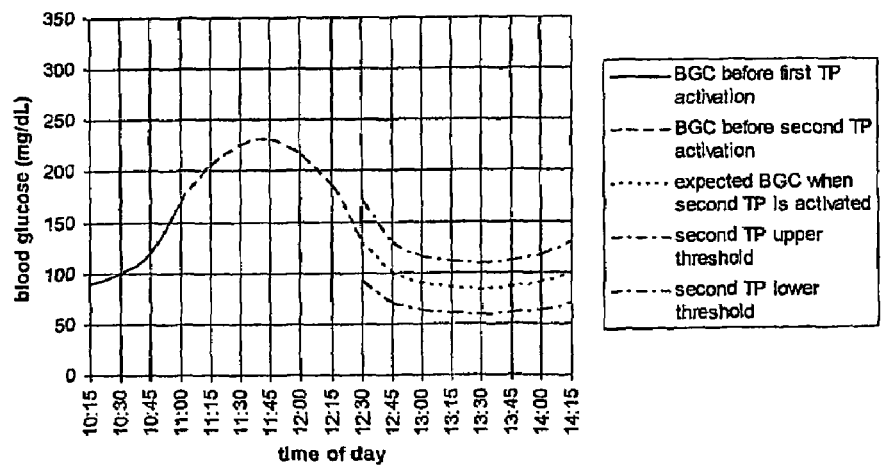

Donna manages her diabetes with insulin injections and a continuous glucose monitor that, through a wireless connection, can employ her personal computer as the user interface. Donna eats Sunday brunch at a restaurant where she unknowingly drinks a regular, sugared soft drink, that was mistakenly served to her after she ordered a diet drink. At home at 11:00, upon noticing her high and rising BGC, she injects additional insulin. She types values of expected BGC into her personal computer's threshold profile software to reflect her prediction that the additional insulin will slowly reverse her rising BGC trend and return her BGC to her target range (70-130 mg/dL). She sets her thresholds at 30% above and below the expected BGC function (FIG. 7A). Donna sets up an auditory alarm to alert her if her BGC strays outside of the range defined by the thresholds. Just before 12:30, while still slightly above her target range, Donna's BGC falls below the lower threshold, activating the alarm and indicating that her BGC is falling more rapidly than she had planned, possibly foreshadowing hypoglycemia (FIG. 7B). Donna then programs a new threshold profile with a steeper initial rate of descent and she eats a snack to avoid hypoglycemia (FIG. 7C).

Example 8

Figure 8A:
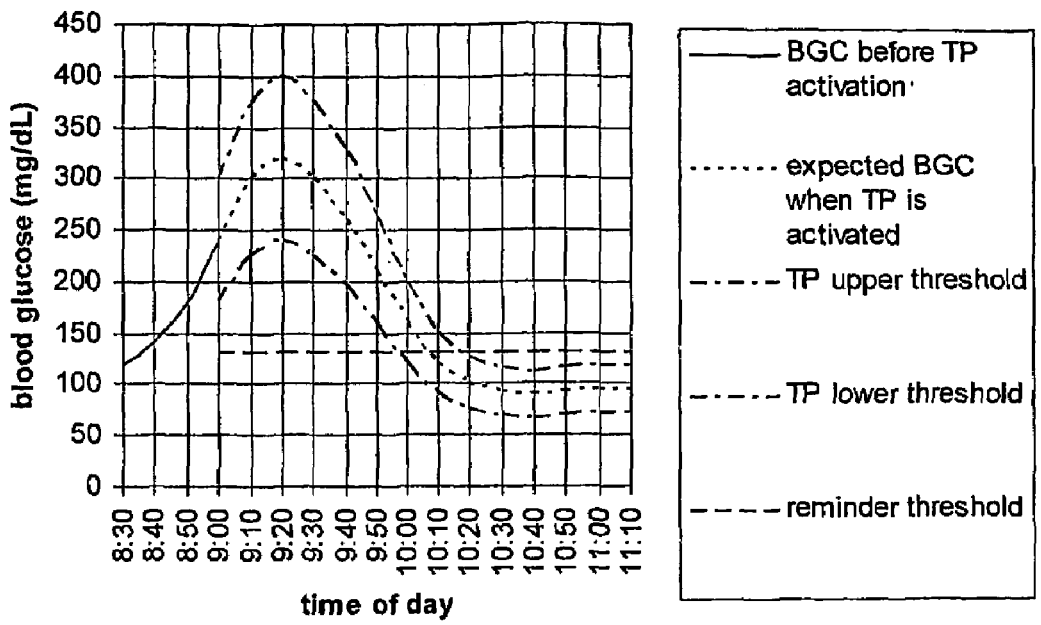
FIGS. 8A and 8B depict a threshold profile established by a user and a BGC level in relation to the threshold profile over time. See Example 8 for details.
Figure 8B:
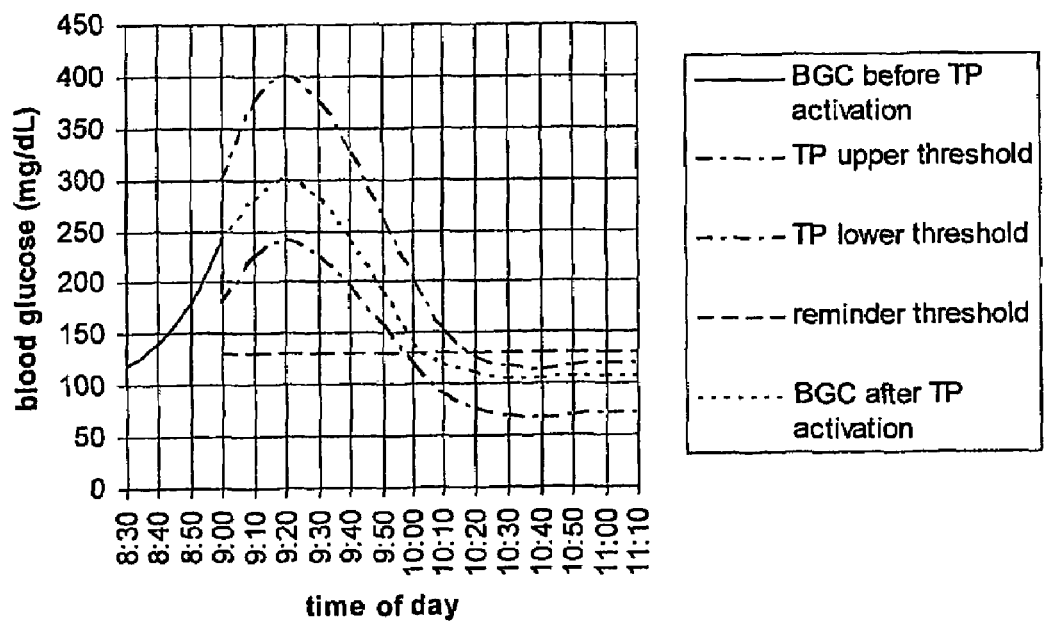

Phil manages his diabetes with an insulin pump and a continuous glucose monitor with a touch pad. After an insulin infusion site failure during his commute to work, Phil treats his high and rising BGC with more than the necessary amount of insulin because he has carbohydrates on hand and he wants to reestablish euglycemia as quickly as possible. At 9:00 he uses the touch pad to spot points of an expected BGC function that includes a very rapid reversal of his rising BGC, followed by a very steep decline that he plans to halt by eating grapes at a point just above his target range (70-120 mg/dL). He sets his thresholds at 25% above and below his expected BGC. Phil sets an alarm to signal if his BGC crosses either of the thresholds, and he sets a reminder chime to alert him that it is time to eat when his BGC falls to 130 mg/dL (FIG. 8A). Phil's BGC follows the anticipated path, the chime rings, and Phil eats his grapes. His BGC then levels out and remains within his target range (FIG. 8B).

Example 9

Figure 9A:
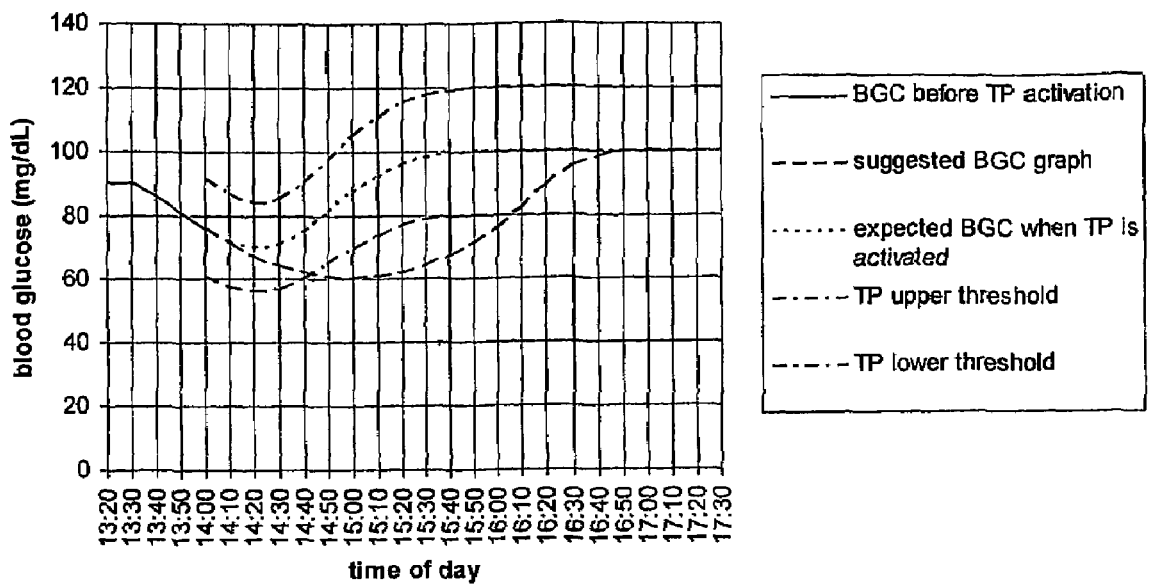
FIGS. 9A and 9B depict a threshold profile established by a user and a BGC level in relation to the threshold profile over time. See Example 9 for details.
Figure 9B:
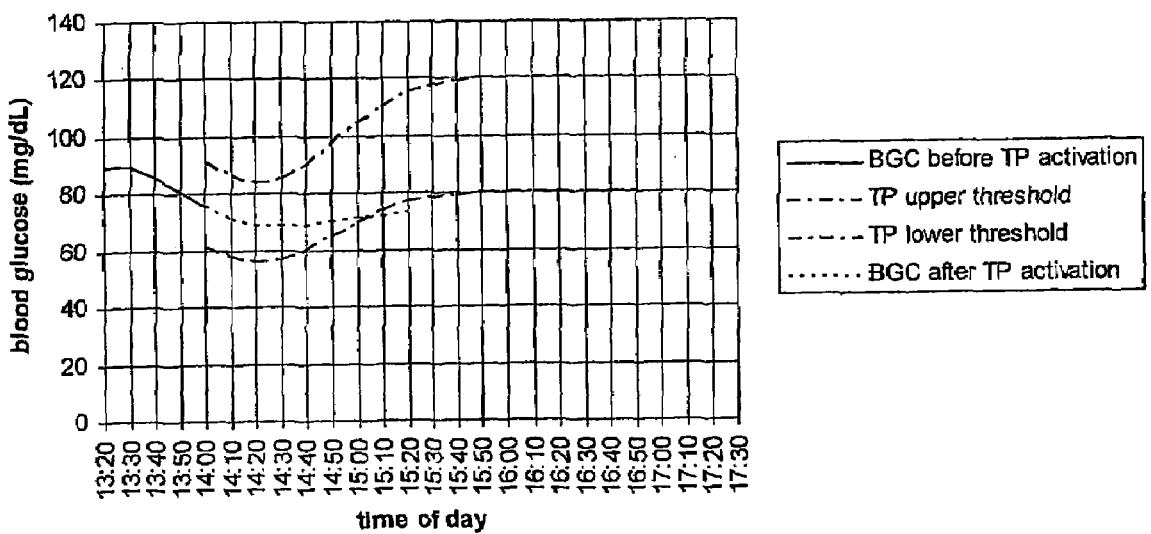

Ned manages his diabetes with an insulin pump and a continuous glucose monitor that share the same user interface component. Ned runs a marathon, and to compensate for the exercise, he decreases his insulin basal rate. Nevertheless, after crossing the finish line, Ned's BGC falls below his target range (80-120 mg/dL). Ned eats two glucose tablets and a piece of fruit. At 14:00 he selects an expected BGC function from a set of several suggested by his pump/monitor, each of which have already been matched to his current BGC and its rate of change. Ned believes that his carbohydrate consumption is more aggressive than what his chosen expected BGC function would suggest, so he adjusts an aggressiveness parameter to simultaneously shorten the time to the BGC minimum, increase the minimum BGC, and shorten the time from the minimum to entry into the target range. Ned leaves the thresholds at the default of 20% above and below the expected BGC, sets an auditory alarm in the event that BGC crosses one of the thresholds, and shortens the threshold profile to provide an automatic reminder to prepare for his next meal (FIG. 9A). It turns out that Ned did not eat enough to raise his BGC as rapidly as expected, and it crosses his lower threshold while rising slowly and still below his target range (FIG. 9B). The alarm sounds, motivating Ned to eat more and program a new threshold profile.

Example 10

Jess helps his daughter manage her diabetes with an insulin pump and a continuous glucose monitor equipped with a wireless auxiliary device. His daughter exercises immediately after a light dinner and her BGC falls below her target range (75-105 mg/dL). Jess suggests that she eat a piece of fruit, and she does. Working on the wireless device at 19:00, Jess selects an expected BGC function and adjusts it to match his daughter's current BGC by proportionally expanding the difference between all points on the selected function and her BGC target (90 mg/dL). He then matches it to his daughter's current rate of BGC change by expansion along the time axis. Next, Jess uses up/down and enter buttons to shift the BGC minimum point and point of entry into the target range to reflect his expectations (FIG. 10A). Jess sets thresholds at 15% above and below the expected BGC, specifies an audible alarm if BGC should cross one of the thresholds, and activates the threshold profile. After his daughter's BGC rises into her target range, it begins to fall again, crosses the lower threshold, and triggers the alarm (FIG. 10B). Jess and his daughter repeat the process of eating fruit and programming a threshold profile that predicts a return to her target range after a brief excursion to lower BGC. This time, the threshold profile expires without incident while his daughter is asleep, and Jess allows the glucose monitor to revert to a default threshold profile with thresholds equal to the bounds of her target range.

Example 11

Figure 11A:
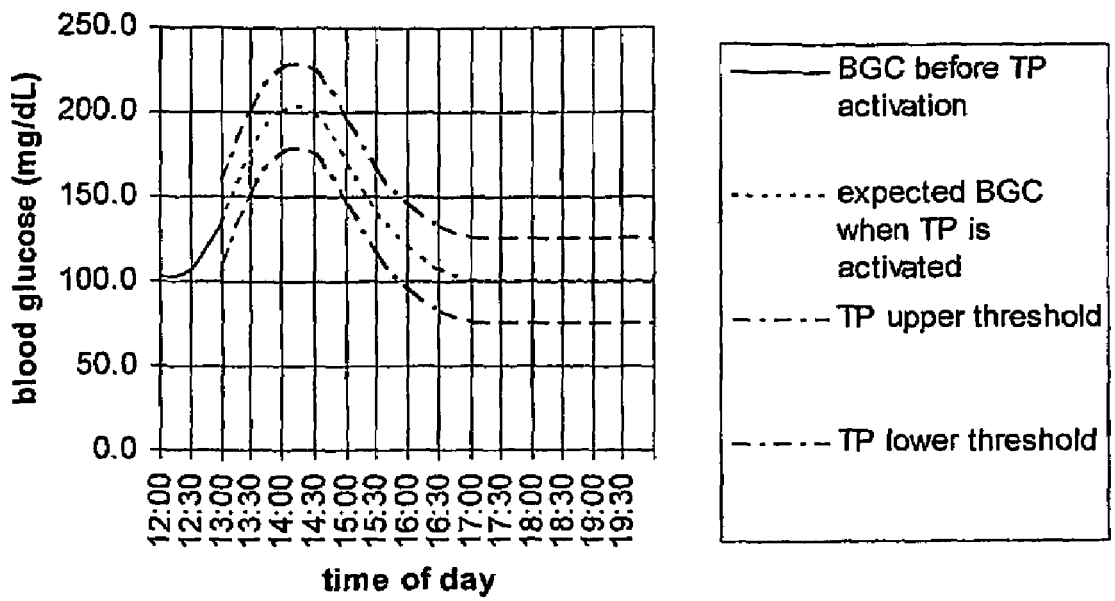
FIGS. 11A and 11B depict a threshold profile established by a user and a BGC level in relation to the threshold profile over time. See Example 11 for details.
Figure 11B:
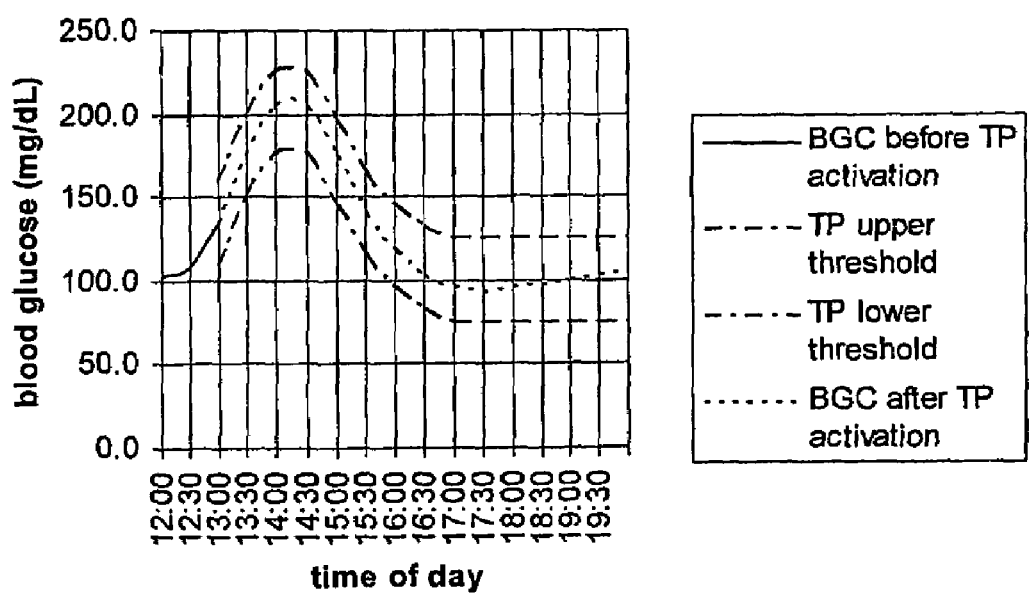

Lisa manages her diabetes with an insulin pump and a continuous glucose monitor, each clipped to her belt. Lisa is very nervous right before playing an afternoon concert in her school orchestra, and she finds her BGC is high and rising. Because she will be performing, Lisa boluses the minimum amount of insulin she could imagine would be sufficient. Then, with a stylus, she draws her expected BGC function on her glucose monitor display screen at 13:00. Lisa's expected BGC graph reflects a slow reversal of the rising trend and a slow return to her target range (75-125 mg/dL) because she has bolused relatively little insulin. She programs thresholds at 25 mg/dL above and below her expected BGC, and she sets her glucose monitor to vibrate if her BGC crosses a threshold (FIG. 11A). Lisa's BGC evolves as she expected through her concert (FIG. 11B), and when her threshold profile expires, she considers how to manage her blood glucose through the post-concert party.

Example 12

Figure 12A:
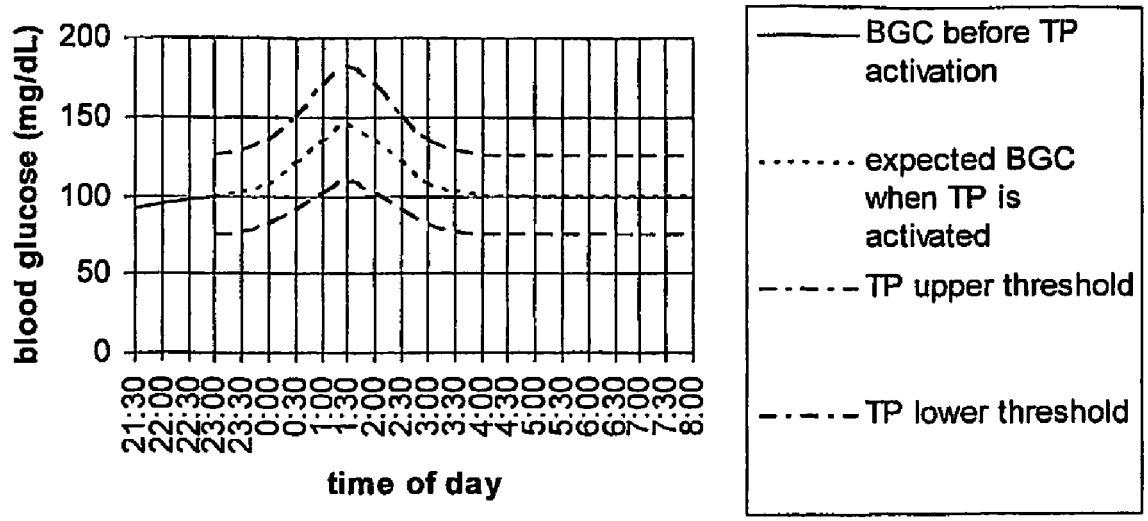
FIGS. 12A and 12B depict a threshold profile established by a user and a BGC level in relation to the threshold profile over time. See Example 12 for details.
Figure 12B:
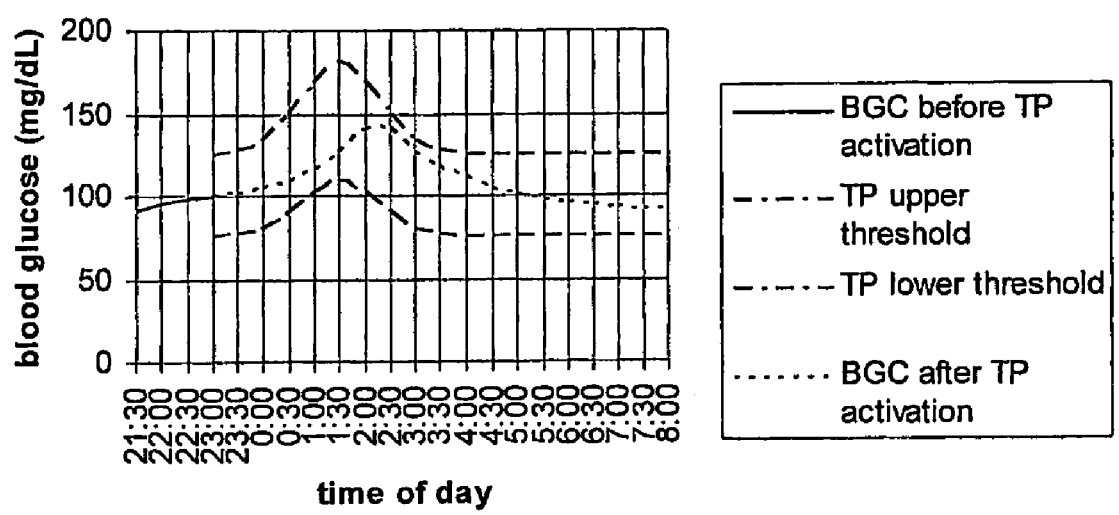

Lauri manages her diabetes with insulin injections and a continuous glucose monitor that, through a wireless connection, can employ her personal computer as the user interface. Lauri attends a late evening college pizza party and counts carbohydrates so skillfully that her BGC remains within her target range (75-125 mg/dL) until her bedtime, 23:00. Experience has taught her that she may require additional insulin at bedtime to moderate an expected rise in BGC that often occurs three hours after eating pizza, so she augments her regular bedtime insulin injection. Lauri uses her personal computer's mouse to draw an expected BGC function that anticipates a small temporary rise in BGC from about midnight to 3:00. She sets her thresholds at 25% above and below her expected BGC, programs an audible alarm in the event that her BGC crosses one of her thresholds, activates her threshold profile, and goes to sleep (FIG. 12A). As anticipated, Lauri's BGC rises above her target range, but then returns to it as specified by her threshold profile (FIG. 12B). Lauri sleeps through the night.

Example 13

Figure 13:
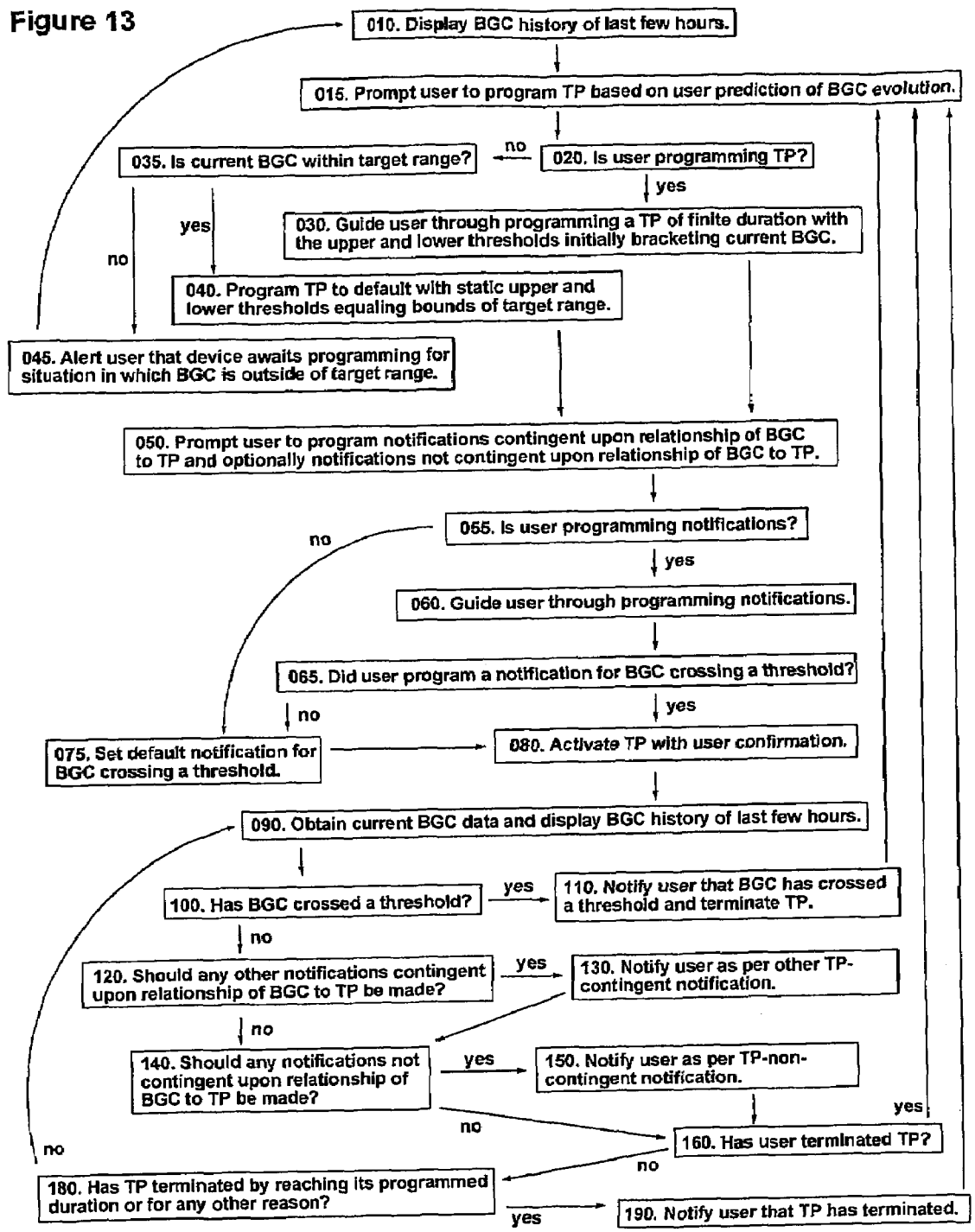
FIG. 13 is a flowchart showing an example, high level, programming scheme of actions that may be taken by a continuous glucose monitoring system that comprises a blood glucose notification threshold profile. See also Example 13.

The following is an example, high level, programming scheme of actions that may be taken by a continuous glucose monitoring system in embodiments of the invention. This programming scheme is meant as a non-limiting illustration. Other schemes are possible within the scope and spirit of embodiments of the invention. This illustration starts from a condition in which no threshold profile (TP) is active. The same programming scheme is also represented in an accompanying flowchart, FIG. 13.

010. Display BGC history of last few hours.
015. Prompt user to program TP based on user prediction of BGC evolution.
020. Is user programming TP?
030. If 020=yes, guide user through programming a TP of finite duration with the upper and lower thresholds initially bracketing current BGC. Go to 050.
035. If 020=no, is current BGC within target range?
040. If 035=yes, program TP to default with static upper and lower thresholds equaling bounds of target range. Go to 050.
045. If 035=no, alert user that device awaits programming for situation in which BGC is outside of target range. Go to 010.
050. Prompt user to program notifications contingent upon relationship of BGC to TP and optionally notifications not contingent upon relationship of BGC to TP.
055. Is user programming notifications?
057. If 055=no, go to 075.
060. If 055=yes, guide user through programming notifications.
065. Did user program a notification for BGC crossing a threshold?
070. If 065=yes, go to 080.
075. Set default notification for BGC crossing a threshold.
080. Activate TP with user confirmation.
090. Obtain current BGC data and display BGC history of last few hours.
100. Has BGC crossed a threshold?
110. If 100=yes, notify user that BGC has crossed a threshold and terminate TP. Go to 015.
120. Should any other notifications contingent upon relationship of BGC to TP be made?
130. If 120=yes, notify user as per other TP-contingent notification.
140. Should any notifications not contingent upon relationship of BGC to TP be made?

150. If 140=yes, notify user as per TP-non-contingent notification.
160. Has user terminated TP?
170. If 160=yes, go to 015.
180. Has TP terminated by reaching its programmed duration or for any other reason?
190. If 180=yes, notify user that TP has terminated. Go to 015.
200. Go to 090.

Example 14

The following is a variant of Example 13 meant to illustrate one of many ways that different programming schemes are possible within the scope and spirit of embodiments of the invention.
010. Display BGC history of last few hours.
015. Prompt user to program TP based on user prediction of BGC evolution.
020. Is user programming TP?
030. If 020=yes, guide user through programming a TP of finite duration with the upper and lower thresholds initially bracketing current BGC. Go to 081.
035. If 020=no, is current BGC within target range?
040. If 035=yes, program TP to default with static upper and lower thresholds equaling bounds of target range. Go to 081.
045. If 035=no, alert user that device awaits programming for situation in which BGC is outside of target range. Go to 010.
081. With user confirmation, activate TP with standard notification for BGC crossing a threshold.
090. Obtain current BGC data and display BGC history of last few hours.
100. Has BGC crossed a threshold?
110. If 100=yes, notify user that BGC has crossed a threshold and terminate TP. Go to 015.
160. Has user terminated TP?
170. If 160=yes, go to 015.
180. Has TP terminated by reaching its programmed duration or for any other reason?
190. If 180=yes, notify user that TP has terminated. Go to 015.
200. Go to 090.

Embodiments of the present invention should not be considered limited to the particular examples described above, but rather should be understood to cover all aspects of the invention as fairly set out in the attached claims. Various modifications to, and equivalents and alternative forms of, the specifics described above fall within the scope and spirit of the present invention, as will be readily apparent to those having skill in the art to which the invention is directed. The claims are intended to cover all such modifications, equivalents, and alternative forms.

What is claimed is:

1. A continuous blood glucose monitoring system comprising:
a system configured to continuously receive data from blood glucose monitoring sensors;
the system configured to convert sensor data into current blood glucose concentration values;
the system configured to support continuously fluctuating blood glucose notification threshold profiles;
the continuously fluctuating blood glucose notification threshold profiles comprising:
an upper blood glucose concentration threshold function;
a lower blood glucose concentration threshold function;
the threshold functions comprising specific values at specific times;
the threshold functions comprising functions of expected blood glucose concentration as a function of time;
the threshold functions comprising the bounds of an expected blood glucose concentration range;
the system configured to compare a current blood glucose concentration value with a corresponding upper blood glucose concentration threshold value;
the system configured to compare a current blood glucose concentration value with a corresponding lower blood glucose concentration threshold value;
the system configured to alert a user when a current blood glucose concentration value is greater than a corresponding upper blood glucose concentration threshold value;
and the system configured to alert a user when a current blood glucose concentration value is less than a corresponding lower blood glucose concentration threshold value.

2. The system of claim 1 configured to alert a user when one or more events comprising:
a predetermined period of time passing since threshold profile activation;
a predetermined time of day occurring;
a user maintaining current blood glucose concentration within the threshold profile range for a predetermined period of time;
a rate of change of current blood glucose concentration exceeding a threshold rate of change;
a rate of change of current blood glucose concentration falling below a threshold rate of change;
a current blood glucose concentration percentage rate of change exceeding a threshold percentage rate of change;
a current blood glucose concentration percentage rate of change falling below a threshold percentage rate of change;
a second derivative of current blood glucose concentration exceeding a threshold second derivative of blood glucose concentration;
a second derivative of current blood glucose concentration falling below a threshold second derivative of blood glucose concentration;
occurs.

3. The system of claim 2 wherein the alert comprises one or more of: a visual alert; an auditory alert; a tactile alert.

4. The system of claim 1 further comprising a graphic display capable of displaying one or more graphs comprising:
a graph of an upper blood glucose concentration threshold function;
a graph of a lower blood glucose concentration threshold function;
a graph of an expected blood glucose concentration function;
a graph of measured blood glucose concentration.

5. The system of claim 4 wherein
a graph of an upper blood glucose concentration threshold function is displayed in a first color;
a graph of a lower blood glucose concentration threshold function is displayed in a second color;
a graph of an expected blood glucose concentration function is displayed in a third color;
a graph of measured blood glucose concentration is displayed in a fourth color.

6. The system of claim 5 wherein the first color and the second color are the same color.

7. The system of claim 1 further comprising a data store configured to support storage and retrieval of blood glucose-related data.

8. The system of claim 7 wherein the data are labeled.

9. The system of claim 7 configured to allow a user to define a blood glucose threshold profile by using a method comprising one or more steps of:
- the step of retrieving a blood glucose threshold profile from a data store;
- the step of retrieving a blood glucose threshold profile from a data store and the further step of modifying the blood glucose threshold profile;
- the step of retrieving an expected blood glucose concentration function from a data store;
- the step of retrieving an expected blood glucose concentration function from a data store and the further step of modifying the expected blood glucose concentration function;
- the step of retrieving an upper blood glucose concentration threshold function from a data store;
- the step of retrieving an upper blood glucose concentration threshold function from a data store and the further step of modifying the upper blood glucose concentration threshold function;
- the step of retrieving a lower blood glucose concentration threshold function from a data store;
- the step of retrieving a lower blood glucose concentration threshold function from a data store and the further step of modifying the lower blood glucose concentration threshold function.

10. The system of claim 7 configured to allow a user to define a blood glucose threshold profile by:
- the system analyzing recent measured blood glucose concentration data;
- the system retrieving from a data store at least one blood glucose-related data item based upon the analysis of recent measured blood glucose concentration data, wherein the at least one data item comprises one or more of:
  - a threshold profile data item;
  - an upper blood glucose concentration threshold function data item;
  - a lower blood glucose concentration threshold function data item;
  - an expected blood glucose concentration function data item;
- the system optionally modifying the at least one blood glucose-related data item based upon the analysis of recent measured blood glucose concentration data;
- the system presenting the at least one blood glucose-related data item to the user;
- the system allowing the user to select a blood glucose-related data item;
- and the system optionally allowing the user to modify the selected blood glucose-related data item.

11. The system of claim 1 configured to allow a user to define a blood glucose threshold profile by a method comprising one or more steps of:
- the step of drawing the graph of an upper blood glucose concentration threshold function using a device capable of accepting graphic input;
- the step of drawing the graph of a lower blood glucose concentration threshold function using a device capable of accepting graphic input;
- the step of spotting points defining an upper blood glucose concentration threshold function using a device capable of accepting graphic input;
- the step of spotting points defining a lower blood glucose concentration threshold function using a device capable of accepting graphic input;
- the step of entering numeric data defining an upper blood glucose concentration threshold function using a device capable of accepting numeric input;
- the step of entering numeric data defining a lower blood glucose concentration threshold function using a device capable of accepting numeric input;
- the step of drawing a graph of an expected blood glucose concentration function using a device capable of accepting graphic input;
- the step of spotting points defining an expected blood glucose concentration function using a device capable of accepting graphic input;
- the step of entering numeric data defining an expected blood glucose concentration function using a device capable of accepting numeric input.

12. The system of claim 1 wherein the duration of the threshold profile is from about one hour to about twelve hours.

13. A method of using a continuous blood glucose monitoring system comprising the steps of:
- defining a continuously fluctuating blood glucose notification threshold profile comprising:
  - an upper blood glucose concentration threshold function;
  - a lower blood glucose concentration threshold function;
  - the upper and lower blood glucose concentration threshold functions forming the bounds of an expected blood glucose concentration range for the duration of the threshold profile;
  - the threshold functions comprising specific values at specific times;
- activating the threshold profile;
- continuously receiving data from blood glucose monitoring sensors;
- converting the sensor data to current blood glucose concentration values using a processor;
- comparing a current blood glucose concentration value to a corresponding upper blood glucose concentration threshold value;
- comparing a current blood glucose concentration value to a corresponding lower blood glucose concentration threshold value;
- alerting a user if the current blood glucose concentration value is greater than the corresponding upper blood glucose concentration threshold value;
- and alerting a user if the current blood glucose concentration value is less than the corresponding lower blood glucose concentration threshold value.

14. The method of claim 13 further comprising the step of alerting a user when one or more events comprising:
- a predetermined amount of time passing since threshold profile activation;
- a predetermined time of day occurring;
- a user maintaining current blood glucose concentration within the threshold profile range for a predetermined period of time;
- a rate of change of current blood glucose concentration exceeding a threshold rate of change;
- a rate of change of current blood glucose concentration falling below a threshold rate of change;

a current blood glucose concentration percentage rate of change exceeding a threshold percentage rate of change;

a current blood glucose concentration percentage rate of change falling below a threshold percentage rate of change;

a second derivative of current blood glucose concentration exceeding a threshold second derivative of blood glucose concentration;

a second derivative of current blood glucose concentration falling below a threshold second derivative of blood glucose concentration;

occurs.

15. The method of claim 13 wherein the alert comprises one or more of: a visual alert; an auditory alert; a tactile alert.

16. The method of claim 13 further comprising the step of displaying, on a graphic display, one or more graphs comprising:
   a graph of an upper blood glucose concentration threshold function;
   a graph of a lower blood glucose concentration threshold function;
   a graph of an expected blood glucose concentration function;
   a graph of measured blood glucose concentration.

17. The method of claim 16 wherein
   a graph of an upper blood glucose concentration threshold function is displayed in a first color;
   a graph of a lower blood glucose concentration threshold function is displayed in a second color;
   a graph of an expected blood glucose concentration function is displayed in a third color;
   a graph of measured blood glucose concentration is displayed in a fourth color.

18. The method of claim 17 wherein the first color and the second color are the same color.

19. The method of claim 13 further comprising the steps of storing blood glucose-related data in a data store and retrieving blood glucose-related data from a data store.

20. The method of claim 19 wherein the data are labeled.

21. The method of claim 19 further comprising one or more steps of:
   the step of retrieving a blood glucose threshold profile from a data store;
   the step of retrieving a blood glucose threshold profile from a data store and the further step of modifying the blood glucose threshold profile;
   the step of retrieving an expected blood glucose concentration function from a data store;
   the step of retrieving an expected blood glucose concentration function from a data store and the further step of modifying the expected blood glucose concentration function;
   the step of retrieving an upper blood glucose concentration threshold function from a data store;
   the step of retrieving an upper blood glucose concentration threshold function from a data store and the further step of modifying the upper blood glucose concentration threshold function;
   the step of retrieving a lower blood glucose concentration threshold function from a data store;
   the step of retrieving a lower blood glucose concentration threshold function from a data store and the further step of modifying the lower blood glucose concentration threshold function;
whereby the user may define a threshold profile.

22. The method of claim 19 further comprising the steps of:
   the system analyzing recent measured blood glucose concentration data;
   the system retrieving from a data store at least one blood glucose-related data item based upon the analysis of recent measured blood glucose concentration data, wherein the at least one data item comprises one or more of:
      a threshold profile data item;
      an upper blood glucose concentration threshold function data item;
      a lower blood glucose concentration threshold function data item;
      an expected blood glucose concentration function data item;
   the system optionally modifying the at least one blood glucose-related data item based upon the analysis of recent measured blood glucose concentration data;
   the system presenting the at least one blood glucose-related data item to the user;
   the system allowing the user to select a blood glucose-related data item;
   and the system optionally allowing a user to modify the selected data item;
whereby the user may define a threshold profile.

23. The method of claim 13 further comprising one or more steps of:
   the step of drawing the graph of an upper blood glucose concentration threshold function using a device capable of accepting graphic input;
   the step of drawing the graph of a lower blood glucose concentration threshold function using a device capable of accepting graphic input;
   the step of spotting points defining an upper blood glucose concentration threshold function using a device capable of accepting graphic input;
   the step of spotting points defining a lower blood glucose concentration threshold function using a device capable of accepting graphic input;
   the step of entering numeric data defining an upper blood glucose concentration threshold function using a device capable of accepting numeric input;
   the step of entering numeric data defining a lower blood glucose concentration threshold function using a device capable of accepting numeric input;
   the step of drawing a graph of an expected blood glucose concentration function using a device capable of accepting graphic input;
   the step of spotting points defining an expected blood glucose concentration function using a device capable of accepting graphic input;
   the step of entering numeric data defining an expected blood glucose concentration function using a device capable of accepting numeric input.

24. The method of claim 13 wherein the duration of the threshold profile is from about one to about twelve hours.

25. A computer readable medium comprising executable processor code configured to support a continuous blood glucose monitoring system;
   the code comprising:
      code for receiving data from continuous blood glucose monitoring sensors;
      code for converting blood glucose sensor data into current blood glucose concentration values;
      code supporting continuously fluctuating blood glucose notification threshold profiles;

the threshold profiles comprising:
an upper blood glucose concentration threshold function;
a lower blood glucose concentration threshold function;
the threshold functions comprising specific values at specific times;
the threshold functions comprising functions of expected blood glucose concentration as a function of time;
the threshold functions comprising the bounds of an expected blood glucose concentration range;
code for comparing a current blood glucose concentration value with a corresponding upper blood glucose concentration threshold value;
code for comparing a current blood glucose concentration value with a corresponding lower blood glucose concentration threshold value;
code for alerting a user when a current blood glucose concentration is greater than a corresponding upper blood glucose concentration threshold value;
and code for alerting a user when a current blood glucose concentration is less than a corresponding lower blood glucose concentration threshold value.

26. The computer readable medium of claim 25 further comprising code configured to alert a user when one or more events comprising:
a predetermined period of time passing since threshold profile activation;
a predetermined time of day occurring;
a user maintaining current blood glucose concentration within the threshold profile range for a predetermined period of time;
a rate of change of current blood glucose concentration exceeding a threshold rate of change;
a rate of change of current blood glucose concentration falling below a threshold rate of change;
a current blood glucose concentration percentage rate of change exceeding a threshold percentage rate of change;
a current blood glucose concentration percentage rate of change falling below a threshold percentage rate of change;
a second derivative of current blood glucose concentration exceeding a threshold second derivative of blood glucose concentration;
a second derivative of current blood glucose concentration falling below a threshold second derivative of blood glucose concentration;
occurs.

27. The computer readable medium of claim 26 wherein the alert comprises one or more of: a visual alert; an auditory alert; a tactile alert.

28. The computer readable medium of claim 25 further comprising code supporting a graphic display capable of displaying one or more graphs comprising:
a graph of an upper blood glucose concentration threshold function;
a graph of a lower blood glucose concentration threshold function;
a graph of an expected blood glucose concentration function;
a graph of measured blood glucose concentration.

29. The computer readable medium of claim 28 further comprising code wherein:
a graph of an upper blood glucose concentration threshold function is displayed in a first color;
a graph of a lower blood glucose concentration threshold function is displayed in a second color;
a graph of an expected blood glucose concentration function is displayed in a third color;
a graph of measured blood glucose concentration is displayed in a fourth color.

30. The computer readable medium of claim 29 further comprising code wherein the first color and the second color are the same color.

31. The computer readable medium of claim 25 further comprising code supporting a data store configured to support storage and retrieval of blood glucose-related data.

32. The computer readable medium of claim 31 further comprising code supporting labeled data.

33. The computer readable medium of claim 31 further comprising code configured to allow a user to define a blood glucose threshold profile by using a method comprising one or more steps of:
the step of retrieving a blood glucose threshold profile from a data store;
the step of retrieving a blood glucose threshold profile from a data store and the further step of modifying the blood glucose threshold profile;
the step of retrieving an expected blood glucose concentration function from a data store;
the step of retrieving an expected blood glucose concentration function from a data store and the further step of modifying the expected blood glucose concentration function;
the step of retrieving an upper blood glucose concentration threshold function from a data store;
the step of retrieving an upper blood glucose concentration threshold function from a data store and the further step of modifying the upper blood glucose concentration threshold function;
the step of retrieving a lower blood glucose concentration threshold function from a data store;
the step of retrieving a lower blood glucose concentration threshold function from a data store and the further step of modifying the lower blood glucose concentration threshold function.

34. The computer readable medium of claim 31 further comprising code configured to allow a user to define a blood glucose threshold profile;
the code comprising:
code for analyzing recent measured blood glucose concentration data;
code for retrieving from a data store at least one blood glucose-related data item based upon the analysis of recent measured blood glucose concentration data, wherein the at least one data item comprises one or more of:
a threshold profile data item;
an upper blood glucose concentration threshold function data item;
a lower blood glucose concentration threshold function data item;
an expected blood glucose concentration function data item;
code for optionally modifying the at least one blood glucose-related data item based upon the analysis of recent measured blood glucose concentration data;
code for presenting the at least one blood glucose-related data item to the user;
code for allowing the user to select a blood glucose-related data item;

and code for optionally allowing the user to modify the selected blood glucose-related data item.

35. The computer readable medium of claim 25 further comprising code configured to allow a user to define a blood glucose threshold profile by using a method comprising one or more steps of:

the step of drawing the graph of an upper blood glucose concentration threshold function using a device capable of accepting graphic input;

the step of drawing the graph of a lower blood glucose concentration threshold function using a device capable of accepting graphic input;

the step of spotting points defining an upper blood glucose concentration threshold function using a device capable of accepting graphic input;

the step of spotting points defining a lower blood glucose concentration threshold function using a device capable of accepting graphic input;

the step of entering numeric data defining an upper blood glucose concentration threshold function using a device capable of accepting numeric input;

the step of entering numeric data defining a lower blood glucose concentration threshold function using a device capable of accepting numeric input;

the step of drawing a graph of an expected blood glucose concentration function using a device capable of accepting graphic input;

the step of spotting points defining an expected blood glucose concentration function using a device capable of accepting graphic input;

the step of entering numeric data defining an expected blood glucose concentration function using a device capable of accepting numeric input.

36. The computer readable medium of claim 25 further comprising code to support a threshold profile duration from about one hour to about twelve hours.

* * * * *